US012788721B2

(12) United States Patent
Bradbury et al.

(10) Patent No.: US 12,788,721 B2
(45) **Date of Patent: *Nov. 10, 2026**

(54) MULTI-COMPONENT PACKAGED DOSAGE FORM AND METHOD

(71) Applicant: APRECIA PHARMACEUTICALS LLC, Mason, OH (US)

(72) Inventors: Thomas J. Bradbury, Yardley, PA (US); Aleece M. Phillips, Yardley, PA (US); Thomas G. West, Lawrenceville, NJ (US); Jaedeok Yoo, Princeton, NJ (US); Munhee Lee, Princeton, NJ (US); Henry Cabral, Hillsborough, NJ (US)

(73) Assignee: APRECIA PHARMACEUTICALS LLC, Mason, OH (US)

(*) Notice: Subject to any disclaimer, the term of this patent is extended or adjusted under 35 U.S.C. 154(b) by 814 days.

This patent is subject to a terminal disclaimer.

(21) Appl. No.: 17/919,087

(22) PCT Filed: Apr. 15, 2021

(86) PCT No.: PCT/US2021/027558

§ 371 (c)(1),
(2) Date: Oct. 14, 2022

(87) PCT Pub. No.: WO2021/211898

PCT Pub. Date: Oct. 21, 2021

(65) Prior Publication Data

US 2023/0190661 A1 Jun. 22, 2023

Related U.S. Application Data

(60) Provisional application No. 63/010,628, filed on Apr. 15, 2020.

(51) Int. Cl.
*A61K 9/20* (2006.01)

(52) U.S. Cl.
CPC .......... *A61K 9/2095* (2013.01); *A61K 9/2086* (2013.01)

(58) Field of Classification Search
CPC .... A61K 9/2095; A61K 9/2086; A61K 9/141; A61J 1/035; A61J 3/06
See application file for complete search history.

(56) References Cited

U.S. PATENT DOCUMENTS

| | | | | |
|---|---|---|---|---|
| 2,415,859 | A * | 2/1947 | Ancker | B65D 75/54 206/539 |
| 4,258,027 | A | 3/1981 | Ullman et al. | |
| 4,305,502 | A | 12/1981 | Gregory et al. | |
| 4,631,837 | A | 12/1986 | Magoon | |
| 5,343,672 | A | 9/1994 | Kearney et al. | |
| 6,047,484 | A | 4/2000 | Bolland et al. | |
| 6,149,940 | A * | 11/2000 | Maggi | A61K 31/517 514/777 |
| 6,471,992 | B1 | 10/2002 | Yoo et al. | |
| 6,669,769 | B2 | 12/2003 | Smith | |
| 6,945,638 | B2 | 9/2005 | Teung et al. | |
| 6,990,748 | B2 | 1/2006 | Magoon et al. | |
| 7,300,668 | B2 | 11/2007 | Pryce Lewis et al. | |
| 7,875,290 | B2 | 1/2011 | Payumo et al. | |
| 8,088,415 | B2 | 1/2012 | Wang et al. | |
| 8,516,714 | B2 | 8/2013 | Biemans et al. | |
| 8,802,145 | B2 | 8/2014 | Bauer | |
| 8,974,825 | B2 | 3/2015 | Jahagirdar et al. | |
| 9,096,335 | B2 | 8/2015 | Ahuja et al. | |
| 9,314,429 | B2 | 4/2016 | Jacob et al. | |
| 9,339,489 | B2 | 5/2016 | Jacob et al. | |
| 9,409,699 | B2 | 8/2016 | Weigel | |
| 9,427,399 | B2 | 8/2016 | Adams et al. | |
| 9,445,971 | B2 | 9/2016 | Anderson et al. | |
| 9,492,380 | B2 | 11/2016 | Jacob et al. | |
| 9,828,119 | B2 | 11/2017 | Wolf | |

(Continued)

FOREIGN PATENT DOCUMENTS

| | | | |
|---|---|---|---|
| CN | 104760767 | A | 7/2015 |
| CN | 107412177 | A | 12/2017 |

(Continued)

OTHER PUBLICATIONS

Aprecia, "Additive Manufacturing: 3D-Printed Pills", Mar. 20, 2020, https://aprecia.com/resources/additive-manufacturing-3d-printed-pills/ (40 pages).
First Office Action dated Apr. 10, 2025 in related European Appl. No. 21788586.2 filed Oct. 20, 2022 (7 pages).
First Office Action dated Apr. 24, 2025 in related Chinese Appl. No. 202180036266.X filed Nov. 18, 2022 (6 pages) with translation (5 pages).
First Office Action dated Jun. 10, 2025 in related Japanese Appl. No. 2022-562660 filed Oct. 14, 2022 (5 pages) with JPO machine translation (5 pages).
First Office Action dated Dec. 11, 2024 in related Chinese Appl. No. 202310287787.3 filed Mar. 22, 2023 (7 pages) with Google machine translation (4 pages).

(Continued)

*Primary Examiner* — David Browe
(74) *Attorney, Agent, or Firm* — Daniel F. Nesbitt; Nesbitt IP LLC

(57) ABSTRACT

A method and system of forming a pharmaceutical dosage form within a portion of a blister packaging. The method includes the steps of providing a blister packaging for the dosage form with depressions. A predetermined amount of a drug-containing powder material comprising drug-containing particles is deposited into a substantially uniform powder layer within the depressions. A binding liquid is then deposited in a pattern on the powder layer within the depressions, to bind the particles of the powder layer and form an incremental wetted powder layer. Excess solvent in the binding material can be removed to form an incremental bound layer. These steps are repeated in sequence at least one or more times to form the pharmaceutical dosage form within the blister packaging.

16 Claims, 9 Drawing Sheets

(56) References Cited

U.S. PATENT DOCUMENTS

| | | | | |
|---|---|---|---|---|
| 9,833,955 | B2 | 12/2017 | Muller et al. | |
| 10,071,372 | B2 | 9/2018 | Nitsch | |
| 10,421,265 | B2 | 9/2019 | Houben et al. | |
| 11,278,501 | B2 * | 3/2022 | Beach-Herrera | A61J 3/06 |
| 2003/0228368 | A1 | 12/2003 | Wynn et al. | |
| 2006/0283758 | A1 | 12/2006 | Pasbrig | |
| 2008/0073372 | A1 | 3/2008 | Keller | |
| 2008/0311191 | A1 | 12/2008 | Nangia et al. | |
| 2009/0060983 | A1 | 3/2009 | Bunick et al. | |
| 2010/0016348 | A1 | 1/2010 | Bunick et al. | |
| 2010/0316712 | A1 | 12/2010 | Nangia et al. | |
| 2012/0217182 | A1 | 8/2012 | Liebenberg et al. | |
| 2014/0065194 | A1 | 3/2014 | Yoo et al. | |
| 2014/0271862 | A1 | 9/2014 | Jacob et al. | |
| 2016/0082658 | A1 | 3/2016 | Swartz et al. | |
| 2017/0188616 | A1 | 7/2017 | Alfiere et al. | |
| 2017/0312179 | A1 | 11/2017 | Gamberini | |
| 2017/0322068 | A1 | 11/2017 | Gueller et al. | |
| 2018/0031410 | A1 | 2/2018 | Lux et al. | |
| 2018/0141275 | A1 | 5/2018 | Patel et al. | |
| 2018/0319519 | A1 | 11/2018 | Stange et al. | |
| 2019/0142743 | A1 | 5/2019 | Fuisz et al. | |

FOREIGN PATENT DOCUMENTS

| | | | |
|---|---|---|---|
| JP | H07-508676 | A | 9/1995 |
| JP | H09-508587 | A | 9/1997 |
| JP | 2006-298394 | A | 11/2006 |
| JP | 2008-517979 | A | 5/2008 |
| JP | 2010-538002 | A | 12/2010 |
| JP | 2018-526289 | A | 9/2018 |
| WO | 9412142 | | 6/1994 |
| WO | 9412142 | A1 | 6/1994 |
| WO | 9635566 | A1 | 11/1996 |
| WO | 0328990 | A1 | 4/2003 |
| WO | 2006045830 | A1 | 5/2006 |
| WO | 2014039378 | | 3/2014 |
| WO | 2014138603 | A1 | 9/2014 |
| WO | 2015159300 | A1 | 10/2015 |
| WO | 2017034951 | A1 | 3/2017 |
| WO | 2018206497 | A2 | 11/2018 |
| WO | 2020081561 | A1 | 4/2020 |

OTHER PUBLICATIONS

Alhnan et al., "Emergence of 3D Printed Dosage Forms: Opportunities and Challenges", 2016, Pharm Res. vol. 33, p. 1817-1832 (16 pages).

Norman, et al., "A new chapter in pharmaceutical manufacturing: 3D-printed drug products.", Jan. 1, 2017, Advanced Drug Delivery Reviews vol. 108, p. 39-50 (12 pages).

"Vibrating Tables", Tinsley Equipment Company, Apr. 3, 2012, https://www.tinsleycompany.com/bulk-process-equipment/vibratory-process-equipment/vibrating-tables/ (6 pages).

"Flex PowderDose", ChemSpeed Technologies Inc., Aug. 17, 2017, https://www.chemspeed.com/flexpowderdose/ (5 pages).

Jamroz et al., "3D Printing in Pharmaceutical and Medical Applications—Recent Achievements and Challenges", Pharm Res, vol. 35, No. 176, Jul. 11, 2018 (22 pages).

"Solid surface energy data (SFE) for common polymers", Surface-tension.de, Dec. 5, 2004, http://www.surface-tension.de/solid-surface-energy.htm (2 pages).

International Search Report with Written Opinion dated Oct. 6, 2021 by the International Searching Authority for corresponding International Application No. PCT/US2021/027558, filed Apr. 15, 2021 (15 pages).

International Preliminary Report on Patentability (Chapter I) dated Oct. 27, 2022 by the International Searching Authority for corresponding International Application No. PCT/US2021/027558, filed Apr. 15, 2021 (11 pages).

Beach-Herrera, et al., U.S. Appl. No. 17/285,186, filed Apr. 14, 2021 (now U.S. Pat. No. 11,278,501 issued (Mar. 22, 2022).

Beach-Herrera, et al., U.S. Appl. No. 17/685,185, filed Mar. 2, 2022.

Final Office Action dated Apr. 7, 2026 in related Japanese Appl. No. 2022-562660 filed Oct. 14, 2022 (3 pages) with JPO machine translation (3 pages).

* cited by examiner

MULTI-COMPONENT PACKAGED DOSAGE FORM AND METHOD

CROSS-REFERENCE TO RELATED APPLICATIONS

The present application is a National Stage Entry of International Application Number PCT/US2021/027558, filed Apr. 15, 2021, which claims the benefit of U.S. Provisional Application No. 63/010,628, filed Apr. 15, 2020, the disclosures of which are hereby incorporated by reference in their entireties.

FIELD OF THE INVENTION

This invention relates to the field of manufacturing of dosage or tablet forms for pharmaceuticals or other active ingredients.

BACKGROUND OF THE INVENTION

In recent years, pharmaceutical producers have turned to the use of blister packs for use in both the forming and dispensing of pharmaceutical tablets. These blister packs generally consist of a blister sheet or blister film and a lidding sheet. The blister sheet contains spatial depressions for containing individual dosages, including tablets, capsule, pills, etc.

Rapid prototyping describes various techniques for fabricating a three-dimensional prototype of an object from a computer model of the object. One technique is three-dimensional printing, whereby a printer is used to fabricate the 3-D prototype from a plurality of two-dimensional layers. In particular, a digital representation of a 3-D object is stored in a computer memory. Computer software sections the representation of the object into a plurality of distinct 2-D layers. Alternatively, a stream (sequential series) of instructions for each incremental layer may be entered directly, e.g. a series of images. A 3-D printer then fabricates a thin layer of bound material for each 2-D image layer sectioned by the software. Together, the layers are printed one on top of the other and adhere to each other to form the desired prototype.

Powder-liquid three-dimensional printing technology has been used to prepare articles such as pharmaceutical dosage forms, mechanical prototypes and concept models, molds for casting mechanical parts, bone growth promoting implants, electronic circuit boards, scaffolds for tissue engineering, responsive biomedical composites, tissue growth promoting implants, dental restorations, jewelry, fluid filters and other such articles.

Three-dimensional printing can include a solid freeform fabrication technique/rapid-prototyping technique in which thin layers of powder are spread onto a surface and selected region of the powder are bound together by the controlled deposition ("printing") of a liquid. This basic operation is repeated layer-by-layer, with each new layer formed on top of and adhered to the previously printed layer, to eventually make three-dimensional objects within a bed of unbound powder. When the printed objects have sufficient cohesion, they may be separated from the unbound powder.

Systems and equipment assemblies for three-dimensional printing of articles are commercially available or in use by others, for example: Massachusetts Institute of Technology Three-Dimensional Printing Laboratory (Cambridge, MA), Z Corporation's (now part of 3D Systems) 3DP and HD3DP™ systems (Burlington, MA), The Ex One Company, L.L.C. (Irwin, PA), Soligen (Northridge, CA), Specific Surface Corporation (Franklin, MA), TDK Corporation (Chiba-ken, Japan), Therics L.L.C. (Akron, OH, now a part of Integra Lifesciences), Phoenix Analysis & Design Technologies (Tempe, AZ), Stratasys, Inc.'s Dimension™ system (Eden Prairie, MN), Objet Geometries (Billerica, MA or Rehovot, Israel), Xpress3D (Minneapolis, MN), and 3D Systems' Invision™ system (Valencia, CA).

Three-dimensional printing systems employing powder and binding liquid typically form articles by depositing binding liquid onto the individual, sequentially-applied layers of the powder. The binding liquid is applied in patterns to predetermined regions of the powder in each powder layer such that unbound powder material remains on the outer periphery of the patterns. The unbound powder typically surrounds the printed articles that are being formed. The printed articles, which comprise bound powder, are then separated from substantial amounts of unbound powder. Such processes undesirably require wasting or recycling the unbound powder. It would be a substantial improvement in the field to provide an equipment assembly, system and method for substantially reducing or eliminating the need to waste or recycle unbound powder.

US Patent Publication 2018/0141275, the disclosure of which is incorporated herein by reference, describes manufacturing systems, equipment assemblies, and use thereof for the preparation of articles by cavity three-dimensional printing. The cavities may be part of build modules on the machine within which articles are formed that approximate the periphery of the cavity. The articles are formed by a succession of plural incremental layers formed within the cavities. Following completion, a 3DP article is discharged from the cavity. The 3DP article is optionally dried, optionally dedusted, and/or optionally packaged.

A further need remains for improved and more convenient pharmaceutical dosage forms, and their method for making.

SUMMARY OF THE INVENTION

The present invention provides a method and system for the forming of a bound-powder or bound-particulate article within a volume of a depression of a packaging material, and for an article of manufacture that is formed in situ within the depression of its packaging. In some embodiments, the article is a dosage form, which can be a medicament, drug, or pharmaceutical tablet or pill, including solid oral prescription drugs. The methods described herein are also referred to as depression three-dimensional printing, or depression 3DP. The packaging can comprise one or more, and in some embodiments a pattern of a plurality of depressions. The method and system can be used for high throughput continuous, semi-continuous, or batch manufacture with minimal product loss, high efficiency, and high product reproducibility.

The embodiments and features described herein provide a method for the formation of pharmaceutical- and drug-containing tablets directly within their packaging, such as a blister pack, and in a particular embodiment, a method for making rapidly-disintegrating pharmaceutical tablets in disposable single-dose blister packs.

The embodiments described herein can provide a substantial reduction in or elimination of waste or recyclable unbound powder as compared to other three-dimensional printing (3DP) processes. Depression 3DP provides for most, substantially all, or all of the particulate material entering a depression to be incorporated into a corresponding single 3-D printed dosage form.

An embodiment of the invention provides a method of forming a dosage form within a portion of a packaging for the dosage form. The method comprises the steps of: providing a portion of a packaging for the dosage form, the portion of the packaging comprising at least one depression; forming in situ within the at least one depression a first powder composition comprising particles into a base powder layer having an upper surface below an upper opening into the depression; depositing a first binding liquid in a continuous pattern on the base powder layer, to bind the particles of the base powder layer to form a base wetted powder layer; forming in situ within the depression a second powder composition comprising particles into an intermediate powder layer having an upper surface below the upper opening, wherein the second powder composition is different from the first powder composition; depositing a second binding liquid in a pattern on the intermediate powder layer along the periphery of the intermediate powder layer, to bind the particles at least along the annular periphery of the intermediate powder layer to form an intermediate wetted powder layer having wetted powder particles at least along the annular periphery; forming in situ within the depression a third powder composition comprising particles into a cap powder layer having an upper surface at or below the upper opening; and depositing a third binding liquid in a continuous pattern on the cap powder layer, to bind the particles of the cap powder layer to form a cap wetted powder layer.

In some embodiments thereof, the intermediate powder layer includes unwetted powder particles of the second powder composition in an interior portion of the intermediate wetted powder layer. In some embodiments thereof, one or more of the base powder layer and the intermediate powder layer has a uniform thickness or substantially uniform thickness. In some embodiments, the base powder layer and the intermediate powder layer comprise a thickness throughout the entire area of the layer that is the same as viewed by the unaided eye.

An embodiment of the invention provides a method of forming a dosage form within a portion of a packaging for the dosage form. The method comprises the steps of: providing a portion of a packaging for the dosage form, the portion of the packaging comprising at least one depression having an upper rim; forming within the at least one depression a first powder composition comprising particles into a base powder layer, wherein an upper surface of the base powder layer is below the upper rim of the depression; depositing a first binding liquid in a continuous pattern on the base powder layer, to bind the particles of the base powder layer to form a base wetted powder layer; forming within the at least one depression a second powder composition comprising particles into an intermediate powder layer, wherein an upper surface of the intermediate powder layer is below the upper rim of the depression, wherein the intermediate powder composition is different from the base powder composition; depositing a second binding liquid in a pattern on the intermediate powder layer along the periphery of the intermediate powder composition, to bind the particles at least along the annular periphery of the intermediate powder layer to form an intermediate wetted powder layer having wetted powder particles at least along the annular periphery; forming within the at least one depression a third powder composition comprising particles into a cap powder layer having a uniform thickness, wherein an upper surface of the cap powder layer is at or below the upper rim of the depression; and depositing a third binding liquid in a continuous pattern on the cap powder layer, to bind the particles of the cap powder layer to form a cap wetted powder layer.

In some embodiments thereof, the intermediate powder layer includes unwetted powder particles of the second powder composition in an interior portion of the intermediate wetted powder layer. In some embodiments thereof, one or more of the base powder layer and the intermediate powder layer has a uniform thickness or substantially uniform thickness.

In any of the various embodiments herein and above, the second powder composition can contain a sensitive active pharmaceutical ingredient (API) or a sensitive particle comprising an API.

In any of the various embodiments herein and above, at least one of the first powder composition and the third powder composition does not contain an API, does not contain a sensitive API, and does not contain a sensitive particle comprising an API. In any of the various embodiments herein and above, the sensitive API is an aqueous-sensitive API, and the sensitive particle is an aqueous-sensitive particle. In any of the various embodiments herein and above, the aqueous-sensitive particle comprising an API comprises a coated API that is coated with a coating material or an agglomerated API that is agglomerated with an agglomerating material.

In any of the various embodiments herein and above, the first binding liquid and the third binding liquid are the same liquid composition. In any of the various embodiments herein and above, the first binding liquid, the second binding liquid, and the third binding liquid are the same liquid composition.

In any of the various embodiments herein and above, the first powder composition and the third powder composition are the same powder composition.

In any of the various embodiments herein and above, the placing of the first powder composition comprises depositing the first powder composition into the base powder layer.

In any of the various embodiments herein and above, the method further includes, prior to placing the first powder composition within the at least one depression, a step of depositing a layer of a binding liquid onto the closed end of the depression.

In any of the various embodiments herein and above, the placing of the first powder composition comprises depositing a predetermined amount of the first powder composition into the depression, and forming the deposited, predetermined amount of the first powder composition into the base powder layer.

In any of the various embodiments herein and above, the placing of the intermediate powder composition comprises depositing the second powder composition into the intermediate powder layer. In any of the various embodiments herein and above, the placing of the intermediate powder composition comprises depositing a predetermined amount of the second powder composition into the depression, and forming the deposited, predetermined amount of the second powder composition into the intermediate powder layer.

In any of the various embodiments herein and above, the placing of the third powder composition comprises depositing the third powder composition into the cap powder layer. In any of the various embodiments herein and above, the placing of the third powder composition comprises depositing a predetermined amount of the third powder composition into the depression, and forming the deposited, predetermined amount of the third powder composition into the cap powder layer.

In any of the various embodiments herein and above, the method further includes a step of drying one or more of the base wetted powder layer, the intermediate wetted powder layer, and the cap wetted powder layer, to remove a portion of a solvent contained within the binding liquid. In any of the various embodiments herein and above, the step of drying the one or more of the base wetted powder layer precedes the step of placing the second powder composition, and the step of drying the one or more of the intermediate wetted powder layer precedes the step of placing the third powder composition.

An embodiment of the invention provides a packaged dosage form, comprising: a packaging for a dosage form comprising at least one depression having an upper rim and a closed end; and a dosage form disposed within the depression, where the dosage form comprises: a base bound powder layer having a plan area and a uniform thickness, comprising particles of a first powder composition bound together with a first binder throughout the plan area and the thickness, an intermediate bound powder layer having a plan area and a uniform thickness, comprising particles of a second powder composition, wherein the particles in the thickness in a peripheral portion of the plan area are bound together with a second binder, and the bound-together peripheral portion of the intermediate bound powder layer is bound at an interface with an upper surface of the base bound powder layer, and the particles within the thickness of an interior portion of the plan area are not bound with the second binder, and a cap bound powder layer having a plan area and a uniform thickness, comprising particles of a third powder composition bound together with a third binder throughout the plan area and the thickness, and the bound-together cap bound powder layer is bound at an interface with an upper surface of the intermediate bound powder layer.

In any of the various embodiments herein and above, the second powder composition contains an aqueous-sensitive API or an aqueous-sensitive particle comprising an API.

In any of the various embodiments herein and above, at least one of the first powder composition and the third powder composition does not contain an API, does not contain a sensitive API, and does not contain a sensitive particle comprising an API. In any of the various embodiments herein and above, the aqueous-sensitive particle comprising an API includes a coated API that is coated with a coating material or an agglomerated API that is agglomerated with an agglomerating material.

In any of the various embodiments herein and above, the first binder and the third binder are the same binder composition. In any of the various embodiments herein and above, the first binder, the second binder, and the third binder are the same binder composition.

In any of the various embodiments herein and above, the first powder composition and the third powder composition are the same powder composition.

In any of the various embodiments herein and above, the base bound powder layer and the intermediate bound powder layer have a bottom face and outer peripheral wall surface that conform to an interior surface of the depression.

The embodiments described herein provide a method of forming a dosage form within a portion of a packaging for the dosage form. The method comprises the steps of: 1) providing a portion of a packaging for the dosage form, the portion of the packaging comprising at least one depression; 2) depositing a predetermined amount of a powder material comprising particles into a powder layer within the at least one depression; 3) depositing a binding liquid in a pattern on the powder layer within the at least one depression, to bind at least a portion of the particles of the powder layer to form an incremental bound layer; and 4) repeating steps 2) and 3) in sequence at least one or more times, thereby forming a dosage form within the portion of the packaging for the dosage form.

The embodiments described herein also provide a method of forming a dosage form within a portion of a packaging for the dosage form, comprising the steps of: 1) providing a portion of a packaging for the dosage form, comprising at least one spatial depression, 2) depositing a predetermined amount of a powder material comprising particles into a powder layer within the at least one depression, 3) depositing a binding liquid in a pattern on the powder layer within the at least one depression, to bind at least a portion of the particles of the powder layer to form an incremental wetted powder layer, and 4) repeating steps 2) and 3) in sequence at least one or more times, thereby forming the dosage form within the portion of the packaging for the dosage form.

In some embodiments, the deposited layer of powder is a substantially uniform powder layer.

In either or both of the above methods, the powder material can be deposited into the at least one depression in a powder depositing region (or system) of an apparatus or system assembly, and the powder material can be layered, or formed into an incremental layer of powder material, in the powder depositing region (or system), or in a dedicated powder leveling region (or system) of an apparatus or system assembly. The binding liquid can be applied to the incremental powder layer when the depression is in a binding liquid application region (or system) of an apparatus or system assembly. The shaping or tamping of a powder material or a wetted powder material layer can be completed in the powder depositing region (or system) or the powder leveling region (or system) of an apparatus or system assembly, or in a dedicated shaping region (or system) of an apparatus or system assembly.

The dosage form packaging comprising the one or more depressions, can be movable between any two or more of the above-mentioned regions (or systems) in any order. In some non-limited embodiments, the receptacle(s) moves: a) from the powder depositing region to the binding liquid application region, repeatedly and then optionally to the shaping region; b) from the powder layering region to the shaping region, and then to the binding liquid application region; c) from the powder layering region to the binding liquid application region then back to the powder layering region and then to the shaping region; or d) from the powder layering region to the powder leveling region, then to the binding liquid application region, then to a drying region. A discharge region can be placed after the powder layering region, the binding liquid application region, the shaping region, and/or the drying region.

The manufactured product package can comprise a film material having one or more depressions therein, the one or more depressions containing a shaped, bound-powder dosage form, formed within the one or more depressions, and a peelable or removable covering sheet adhered to the film material, so as to enclose the dosage form within the one or more depressions.

In an embodiment of the manufactured product package, the dosage form is a bound-powder matrix formed within the one or more depressions by binding a powder deposited within the one or more depressions with a binding liquid.

In an embodiment of the manufactured product package, a portion of the shaped, bound-powder matrix conforms to an inner surface of the one or more depressions.

An embodiment also provides a package comprising a film material having one or more depressions therein, the one or more depressions containing a shaped, bound-powder matrix formed within the one or more depressions, and a peelable covering sheet adhered to the film material, so as to enclose the bound-powder matrix within the one or more depressions.

In an embodiment of the manufactured product package, the bound-powder matrix is formed within the one or more depressions by binding a powder deposited within the one or more depressions with a binding liquid. A portion of the shaped, bound-powder matrix can conform to an inner surface of the one or more depressions. A peripheral portion of the bound-powder matrix that confronts the inner surface of the one or more depressions can include an additional amount of the binding liquid.

In an embodiment of the manufactured product package, the bound-powder matrix comprises a 3D printed, rapidly-dispersible dosage form, and can be formed within the one or more depressions by binding a powder deposited within the one or more depressions with a binding liquid.

In an embodiment of the manufactured product package, the bound-powder matrix comprises an active pharmaceutical ingredient (API).

In various embodiments, a peripheral portion of the bound-powder matrix that confronts the inner surface of the one or more depressions includes an additional amount of a binding liquid; or the at least one depression has a fixed shape and volume, which does not change or vary under ordinary use and handling of the packaging; or the packaging comprises one or more blisters, cups, pods, or other receptacles; or the packaging is pre-formed and/or pre-cut ahead of the dosage-forming process; or the packaging comprises a sheet including a plurality of the depressions formed into the sheet, and where the depression includes a sidewall that extends from the sheet to the closed end; or any combination of one, two, three or more thereof.

In various embodiments, the step 4) above is repeated at least three times.

In various embodiments, a portion of the powder material comprises particles of a binder material, and the binding liquid binds the particles of the binder material.

In various embodiments, the method can include a step, preceding step 2) above, of depositing a binding liquid on at least the closed end of the depression.

In various embodiments, the at least one depression includes an inner surface that includes a release agent.

In various embodiments, the binding liquid comprises a volatile solvent, and the method can include a step of evaporatively removing a portion of the volatile solvent from the incremental bound layer.

In various embodiments, the sidewall has a depression depth, and each powder layer has a thickness of at least 5%, and up to about 100%, and in some embodiments, up to about 50%, of the depression depth. In various embodiments, each layer is about 2% to 50% of the depth of the depression, or about 2% to 30%, or about 2% to 20%, or about 5% to 20%, or about 2% to 10%, or about 5% to 10%, of the depth of the depression.

In some embodiment, the number of powder layers that are deposited into a depression and formed into an incremental bound-powder layer can be one or a plurality of layers, including two or more layers, three or more layers, four or more layers, five or more layers, six or more layers, seven or more layers, or eight or more layers, and up to fifty or fewer layers, forty or fewer layers, thirty or fewer layers, twenty or fewer layers, eighteen or fewer layers, sixteen or fewer layers, fourteen or fewer layers, twelve or fewer layers, ten or fewer layers, eight or fewer layers, six or fewer layers, or four or fewer layers, in any combination.

An incremental powder layer can have a target or weight average thickness, of a predetermined thickness (vertical height). In some embodiments, the predetermined thickness can be varied from 0.005 to 0.015 inches, 0.008 to 0.012 inches, 0.009 to 0.011 inches, about 0.01 inches, 100-300 microns, 100-500 microns, about 200 microns, or about 250 microns. In some embodiments, the thickness of the incremental powder layers range from 100-400 microns, 150-300 microns, or 200-250 microns. In one embodiment, the powder layer thickness is about 200 microns. In another embodiment, the powder layer thickness is about 250 microns.

In some embodiments, the predetermined thickness is at least 0.05 inches, at least 0.008 inches, at least 0.010 inches, at least 0.012 inches, at least 0.014 inches, or at least 0.016 inches, and up to 0.020 inches, up to 0.018 inches, up to 0.016 inches, up to 0.014 inches, up to 0.012 inches, or up to 0.010 inches. As a thicker incremental layer is used, an increasing amount of printing fluid is deposited on that layer to ensure adequate binding both within the plane of the layer and layer-to-layer. Conversely, for a thinner incremental layer, a lesser amount of printing fluid is deposited to obtain the same extent of binding. For a given amount of printing liquid deposited per layer, using a larger layer thickness may reduce (worsen) dosage form handleability and reduce (improve) dispersion time. If too thick of a layer is used for a given amount of fluid, laminar defects may form that cause the dosage form to easily fracture along the plane of the layers (delamination), or the dosage form itself may not have adequate strength to manually or mechanically handled.

Dosage forms produced by a 3DP process described herein can range in diameter (of equivalent diameter of a non-circular area) from about 13-14 mm to about 20-25 mm, and in height (total thickness) from about 5-6 mm to about 8-10 mm.

In an embodiment, the pattern of the binding liquid deposited on the powder layer has a periphery that is disposed against or in contact with the sidewall of the packaging.

In an embodiment, the pattern of the binding liquid deposited on the powder layer has a shape selected from the group consisting of an annular ring and a circle.

In an embodiment, the method can include a step of applying a lidding layer over the dosage form and the at least one depression to form a sealed packaging for the dosage form.

In an embodiment, the binding liquid is deposited by inkjet printing to form the wetted powder layer.

In an embodiment, the step 2) above of depositing the predetermined amount of the powder material comprising particles into the substantially uniform powder layer within the at least one depression, comprises: (i) depositing a predetermined amount of a powder material comprising particles into the at least one depression, and (ii) forming the deposited, predetermined amount of the powder material into a substantially uniform powder layer within the at least one depression.

In an embodiment, the step of forming includes shaping and/or tamping the deposited, predetermined amount of the powder material into the formed powder layer having an upper surface. In another embodiment, the step of forming includes tamping a last deposited, predetermined amount of the powder material into a last formed powder layer having an upper surface.

In an embodiment, the method includes a step, following the step of depositing a binding liquid in a pattern on the powder layer within the at least one depression, comprising shaping and/or tamping of the incremental wetted powder layer into a shaped or tamped wetted powder layer. The formed wetted powder layer has an upper surface that in one embodiment is flat or planar, and in another embodiment is convex or concave.

In an embodiment, the method includes a step, following the formation of a plurality of incremental wetted powder layers into a wetted powder structure comprising multiple wetted layers, comprising a step of shaping and/or tamping the multiple wetted powder layers into a shaped or tamped wetted powder structure.

In an embodiment, the step of shaping and/or tamping employs a stamp or punch. In some embodiments, the stamp or punch has a lower concave surface.

In an embodiment, the powder material can comprise one or more types of drug-containing particles.

The present invention can also provide a 3DP equipment system and assembly for providing and positioning a depression or a pattern of depressions, for example, associated with dosage form packaging, and for the forming of 3DP dosage forms within the depressions. The equipment system and assembly can comprise, without limitation, a powder depositing system, disposed in a powder depositing region, a powder leveling system, disposed in a powder leveling region, a binding liquid application system, disposed in a binding liquid application region, a shaping system, disposed in shaping region, and a drying system, disposed in shaping region.

In some embodiments, the 3DP equipment assembly comprises a control system comprising one or more computerized controllers, one or more computers, and one or more user interfaces for one or more computers. In some embodiments, one or more components of the equipment assembly are computer controlled. In some embodiments, one or more components of the 3DP build system are computer controlled. In some embodiments, the powder depositing system, the powder leveling system, the binding liquid application system, the shaping system, disposed in shaping region, and the drying system, are computer controlled.

In some embodiments, a 3DP equipment assembly can also comprise one or more harvesting systems, one or more liquid removal systems, one or more powder recovery systems, one or more article transfer systems, or one or more inspection systems. The 3DP equipment assembly, apparatus or system can comprise some or all of the above systems. For example, in certain embodiments of a cavity 3DP equipment assembly, apparatus, or system, it is not necessary to have a harvesting system since substantially all of the powder material entering a depression is incorporated into a respective dosage form formed within the depression, with little or no excess powder for separation.

DETAILED DESCRIPTION OF THE INVENTION

Definitions

As used herein, the term “depression” refers to a spatial cavity formed into a portion of a packaging for a dosage form. Non-limiting examples of the depression portion of a packaging include a blister, cup, pod, or other receptacle packaging capable of receiving and containing flowable materials such as powder or liquid.

As used herein, “3DP” means three-dimensional printing, three-dimensionally printed or other such conjugation thereof.

As used herein, “shaping” refers to the act of altering the shape of one or more surfaces of an incremental layer of a material, or the shape of a plurality of one or multiple layers. The altering of the shape can be of the entire surface or of only a portion of the surface, and typically of the upper surface, at the step of shaping. The altered shape can be flat or planar, convex, concave, or any other shape as desired. The altered shape of the upper surface can be different from the shape of the lower surface.

As used herein, the term “tamping” pertains to an act of reducing the porosity or pore volume within a volume of a mass of powder under a force that reduces the volume of the mass of powder. Tamping can be effected with a punch system, whereby a volume of one or more incremental formed layers of powder formed within a depression is shaped and/or reduced.

In describing features herein as pertaining to “any of the various embodiments” or “in various embodiments”, the described feature should be understood to be capable of being combined with any other features and embodiments described within the description, unless such combination or use would be clearly unreasonable or contradict the usefulness or purpose of the described feature.

A process of the invention can comprise one or more tamping steps, one or more shaping steps, and/or one or more marking steps.

As used herein, a “three-dimensional printing build system” or “3DP build system” generally comprises a powder layering system (region), where a powder material is deposited as a layer in a depression or is deposited into a depression and layered into an incremental powder layer within a depression, and a printing system (region), wherein a binding liquid is applied to the incremental powder layer according to a predetermined pattern thereby forming a partially or fully bound powder layer (an incremental printed layer).

Figure 1:
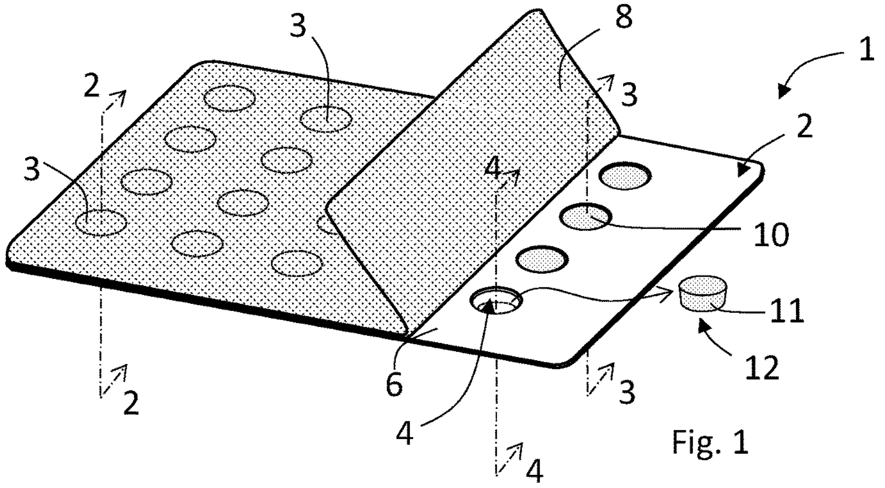
FIG. 1 illustrates a blister pack with a portion of the lidding sheet peeled back, showing dosage forms disposed within the depressions.

FIG. 1 shows a blister pack 1 including a blister sheet 2 in which a desired number of depressions 4 are formed in a sheet 6 of a desired film or laminate material through conventional cold forming. A lidding sheet 8 is shown sealed to the sheet 6 including at locations 3 over depressions that contain a multi-component dosage form 10 (also illustrated in the sectional view of FIG. 2). The front portion of the blister pack 1 illustrates the lidding sheet 8 folded back from over the sheet 6, to illustrate exposing the dosage forms 10 disposed within depressions 4 (illustrated in the sectional view of FIG. 3) or removed from the depressions 4 (illustrated in the sectional view of FIG. 4). The size and shape of the depressions 4 is a matter of choice that can be dictated by the size and nature of the tablet to be formed, as well as other considerations that are well known to those persons skilled in the art. The number and arrangement of the depressions 4 in the blister sheet 2 are a matter of choice or selection that can be based upon the dosage and duration of administration of the tablets, economics, and the type of API active in case of a drug or pharmaceutical tablet, as well as other considerations that are well known to those persons skilled in the art. The film or laminate sheet 6 comprises a formable material into which the one or more depressions can be formed. In one embodiment the film or laminate sheet 6 can comprise a thermoformable plastic layer, for example, polymeric substances including polyamide, polyvinylchloride, polypropylene or other such substances. In another embodiment, the film or laminate sheet 6 can comprise a cold formable metal foil, such as an aluminum film. A laminate material can include two or more layers that can be made of the same or different materials, and the same or different thicknesses. The film or laminated material typically has a thickness between about 25 and 100 microns (μm).

Figure 4:
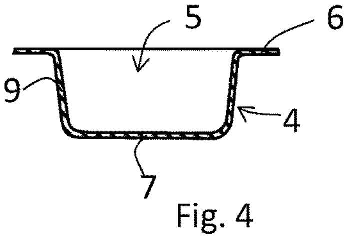
FIG. 4 illustrates a cross-sectional view of a depression from which the dosage form has been removed.

FIG. 4 illustrates a single portion of a blister-type packaging for a dosage form, consisting of a depression 4 formed into the sheet 6 and having a closed end 7 and an outer wall 9 that defines a space 5 within the depression 4. The depressions 4 in the blister sheet 2 are illustrate in a non-limiting embodiment with a circular plan shape and an outer wall tapering inwardly from the sheet toward the closed end 7. Some embodiments of a depression in a blister sheet packaging have elongated shapes, or complex shapes. Some embodiments have outer walls that are rounded, arcuate, or perpendicular with the packaging sheet. A person of ordinary skill would recognize and understand that any embodiment of a packaging material or a depression of any type, shape or size, can be combined, directly and unambiguously, with any other embodiment pertaining to the invention described herein.

Figure 5:
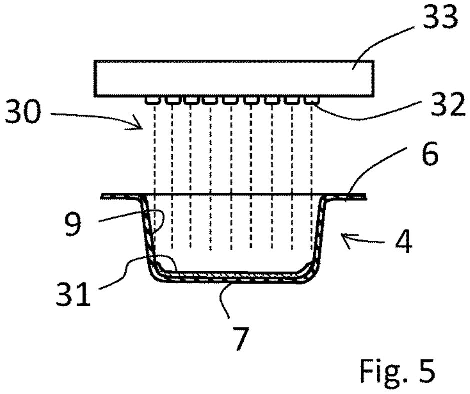
FIG. 5 illustrates a binding liquid being deposited onto the closed end of a depression.

FIG. 5 illustrates an initial, though in some embodiments an optional, step of depositing an initial layer 31 of a binding liquid onto the bottom or closed end 7 of the depression 4, to provide binding of initial powder material 20 that is deposited into the depression 4. The initial layer 31 of a binding liquid can be deposited by spraying droplets 30 of the binding liquid, for example from print nozzles 32 of an inkjet printing nozzle assembly 33. An initial layer or film of binding liquid ensures that a bottom surface of the dosage form 10 securely bonds the particles of the powder material along the bottom surface 12. In some embodiments, an excess amount of binding liquid, more than an amount sufficient to at least bind together the particles of the powder material, is used to form a wetted coating, which when dried or cured forms a hard, resilient bottom coating. In some embodiments, the binding liquid used to form the wetted coating is a different liquid than the binding liquid used for forming the bound powder layers.

Figure 6:
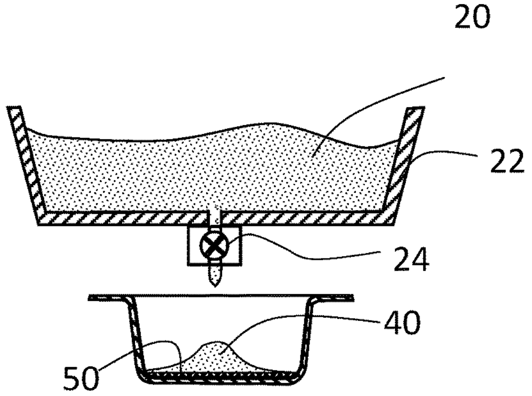
FIG. 6 illustrates depositing a pile of powder material from a powder source into the depression.

FIG. 6 illustrates one of numerous means and methods for depositing a powder material into one or more depressions of a blister-type packaging. FIG. 6 illustrates a step of depositing a first predetermined amount 40 of a powder material 20 comprising particles, within the depression 4 or into each of a plurality of depressions 4. The powder 20 is discharged from a feed container or hopper 22 through a powder-dosing apparatus 24. The powder-dosing apparatus 24 is designed and configured to dispense a predetermined amount 40 of powder from the feed container 22, which can include a predetermined volumetric amount of powder or a predetermined mass amount of powder. In the illustrated embodiment, a predetermined amount of powder 40 is deposited onto the closed end 7 of the depression 4 in the form of a pile 40 of powder. A bottom portion of the first deposited pile 40 of powder 20 is wetted by the optional initial layer 31 of binding liquid, as seen in FIG. 5, to form a coating 50 on the bottom 12 of the dosage form.

In one embodiment, the predetermined amount of powder 40 can be a predetermined volume of a powder material, the powder material having presumably a substantially uniform powder density such that the predetermined volume delivers a substantially fixed mass weight of the powder material. An accurate and reproducible mass weight of a deposited amount of powder material is important to ensure that the finished dosage form, consisting of two or more deposits of the powder material, has a consistent, accurate amount of the total powder material. In an embodiment where the powder material 20 comprises an active ingredient in particulate form, such as a particulate pharmaceutical or drug, and the powder material 20 also comprises one or more other particulate materials, it is preferred that the particulate active ingredient does not segregate from the other particulate materials.

In another embodiment, the predetermined amount of powder can be a predetermined mass weight of a powder material. Again, presuming a substantially uniform powder density, the predetermined mass weight delivers a substantially fixed volume of the powder material. In the illustrated embodiment, the predetermined mass weight of a powder material provides a volume of powder material sufficient to form a substantially uniform powder layer of the fixed volume, within the bottom portion of the available space within the depression 4. This predetermined mass weight or fixed volume of a powder material is also referred to herein as a dose of powder material. Depending on the size and shape of the bottom portion of the available space within the depression 4, a first powder layer consisting of a substantially uniform powder layer of a predeterminable depth is formed.

Various means and apparatus can be used to place or deposit a dose of powder material into a depression. PCT Patent Publication WO2020-081561, the disclosure of which is incorporated by reference in its entirety, discloses in its FIGS. 7 through 10 a manual dosing device comprising a feed container or hopper containing a bulk supply of powder material, an outer cylinder mounted to the bottom of the hopper and having an upper opening communicating with the hopper, and a lower opening, and an inner cylinder that rotates axially within the outer cylinder between a fill rotation position that fills a volumetric fill cavity in the inner cylinder, to a dispensing rotation position at which a volume the powder material within the volumetric void is dispensed gravitationally through the lower opening of the outer cylinder. In some embodiments, the inner cylinder with a fixed-volume fill cavity can be replaced with another inner cylinder having a differently-sized fixed-volume fill cavity for depositing a different predetermined volume of powder. In another embodiment of the invention, the system can include a second (or more) manual dosing device having a fill cavity of a different volumetric size to dispense different predetermined volumes or masses of a powder material. The deposition of powder by gravity into the depression typically creates a pile of powder over the base of the depression, or over the top surface of previously-formed bound powder layer, though usually not in a consistent and reproducible shape, and typically with a tapering of the powder surface towards the outer walls of the depression resulting from the angle of repose of the powder material.

Figure 11:
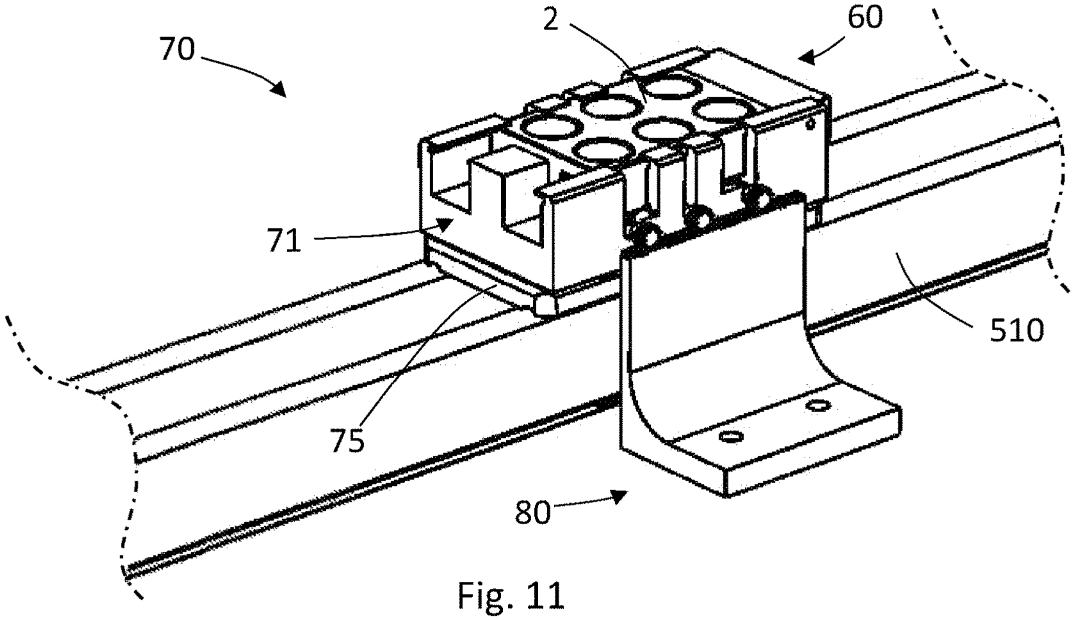
FIG. 11 illustrates a shuttle carriage operating within a leveling region that provides vertical oscillation of a powder dose deposited within depressions of a blister sheet.
Figure 12:
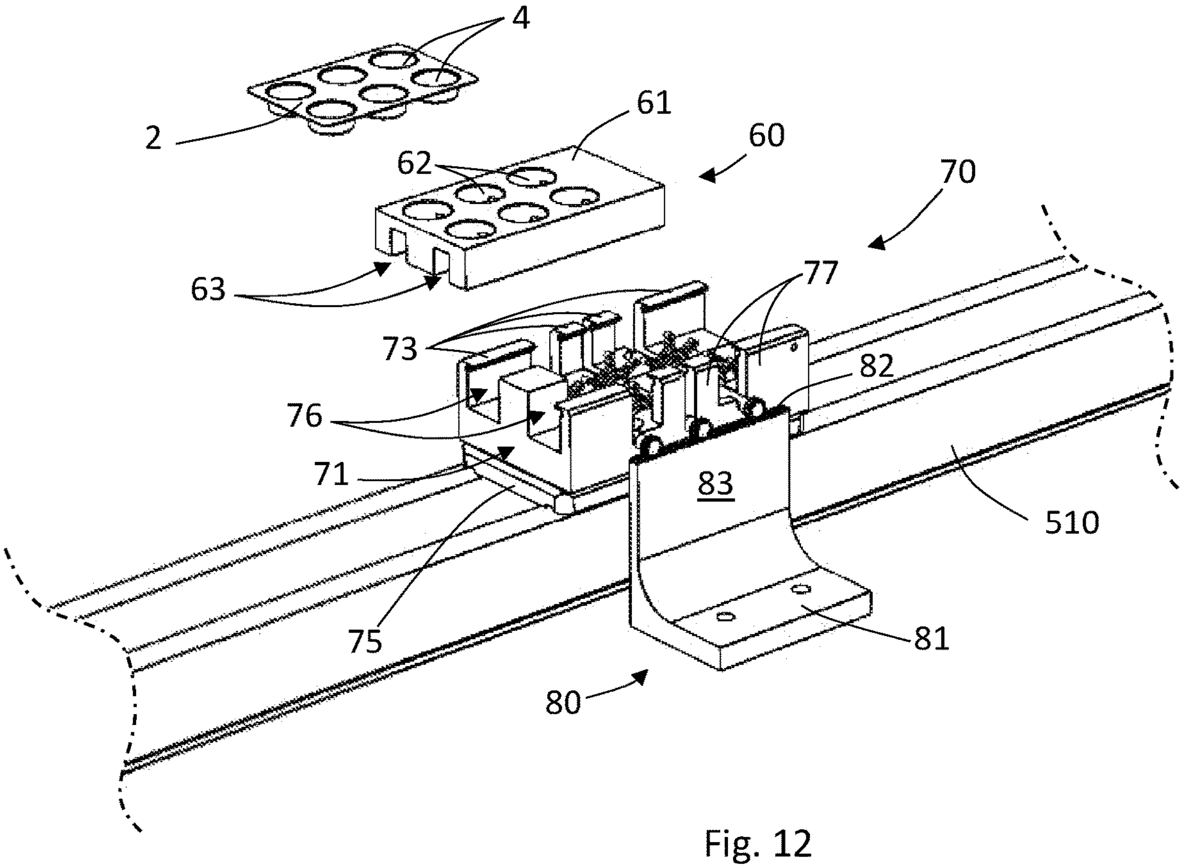
FIG. 12 illustrates the shuttle carriage, a blister sheet support plate, and a blister sheet in an exploded view.
Figure 13:
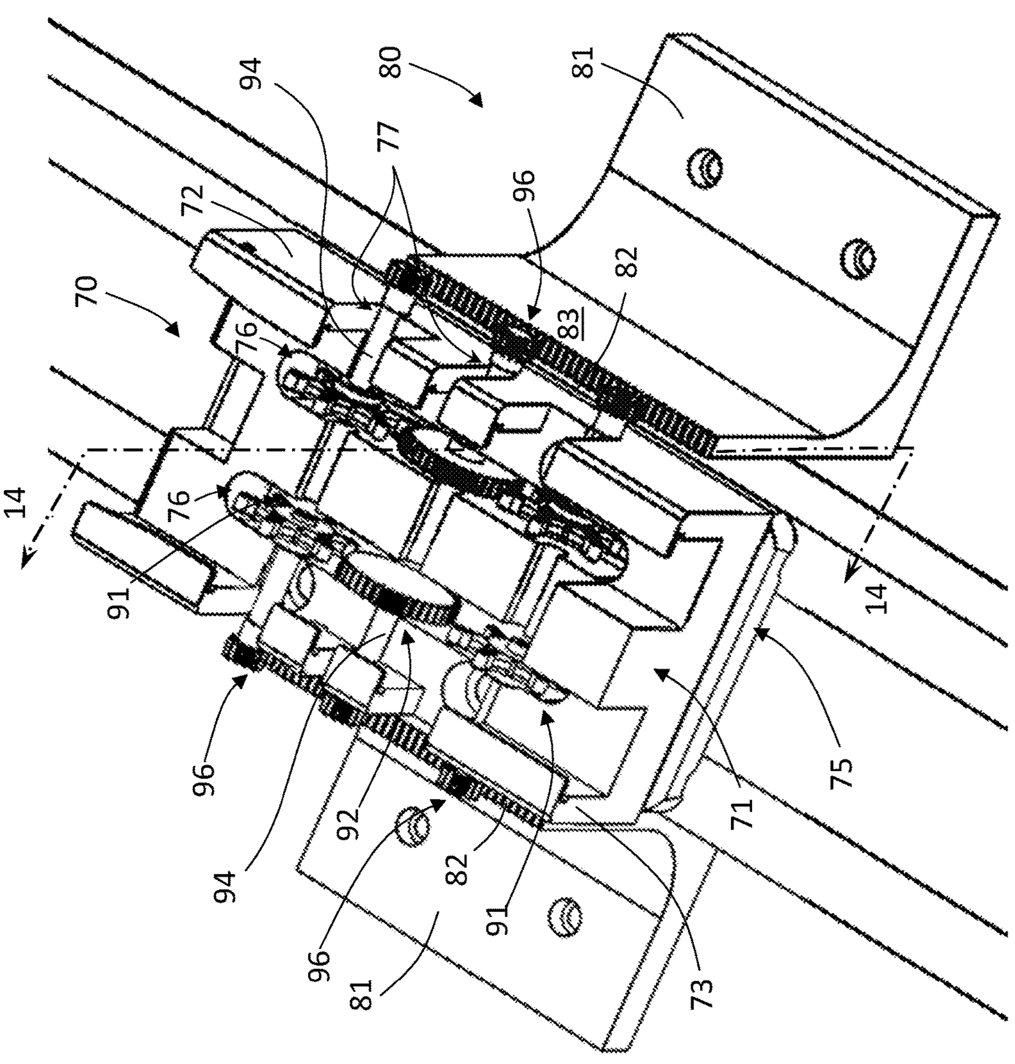
FIG. 13 shows a top perspective view of the shuttle carriage, and illustrates a tapping means for administering vertical oscillation of the powder dose.

The aforementioned PCT Patent Publication WO2020-081561 also shows various automated dosing apparatus for filling a plurality of depressions in a dosing package. A rotary dosing apparatus is shown in its FIGS. 11 through 12B, where a plurality of fill cavities along the outer surface of a rotary dosing drum are filled from a hopper containing a supply of powder material, with the number of fill cavities configured to fill a number of depressions in a blister sheet. In some embodiments of a rotary dosing apparatus, a vacuum system can be included that applies a vacuum upon the inside surface of the fill cavities to assist in maintaining the powder material charged into the fill cavities. Each fill cavity is sufficient in areal size and depth to hold and dispense a dose of powder material into each depression of the blister sheet. In some embodiments, the volumetric rate of powder material into the fill cavities can be throttled using a slide gate or other well-known means for restricting the flow of powder material from the bin. A non-limiting example of a restricting means is a dispensing gate.

FIGS. 13-18 of the aforementioned PCT Patent Publication WO2020-081561 illustrate another embodiment of a slide plate having a volumetric dispensing pocket, the slide plate being slidable laterally between a filling position at which the volumetric dispensing pocket is positioned below the bottom dispensing opening of a powder bin, and a dispensing position at which the volumetric dispensing pocket is positioned above a depression, for dispensing the powder material within the volumetric dispensing pocket directly or indirectly into a depression.

Figure 7:
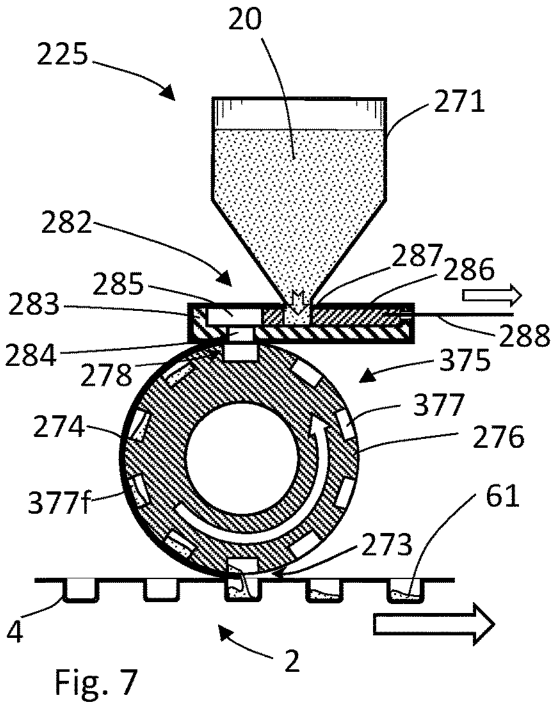
FIG. 7 shows an elevation sectional view through a rotary dosing apparatus and blister sheet.
Figure 8:
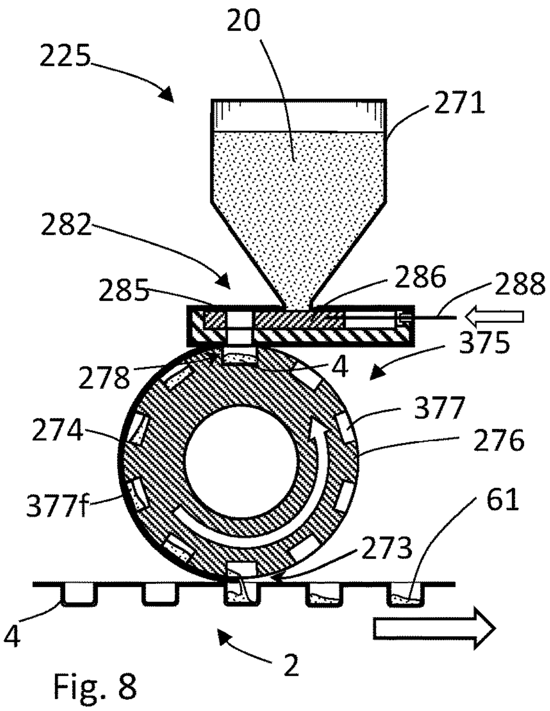
FIG. 8 shows an elevation sectional view through another embodiment of a rotary dosing apparatus and blister sheet.

FIGS. 7 and 8 of the present disclosure illustrate another embodiment of an automated dosing apparatus 225 for filling a plurality of depressions in a dosing package. FIGS. 7 and 8 illustrate that the fill cavities 377 of the rotary dosing apparatus 375 are sufficient in opening size and depth to hold a volume of powder that is in excess of the amount of powder needed to form a powder layer in a depression. In such embodiments, the apparatus 225 also includes a volumetric dispensing pocket to meter a predetermined volume of powder material into the over-sized fill cavity.

An elongated supply bin 271 containing a powder material 20 is oriented along the width of the blister sheet 2, transverse to the direction of movement of the blister sheet 2 beneath the dosing apparatus 225. FIG. 7 illustrates a bottom dispensing opening that feeds powder into a volumetric dispensing pocket 282. In other embodiments, the dispensing opening of the elongated bin can include a powder feeding valve, for example, a rotary feeder, to meter powder material from the bin into a pocket bore 287. The volumetric dispensing pocket 282 includes a support frame 283 having an elongated cavity 285 and a dispensing opening 284 that includes a distal end. A pocket gate 286 is disposed within the elongated cavity 285, and has the pocket bore 287 disposed in a distal portion of the pocket gate 286. A manipulation means extends from a proximal portion of the pocket gate 286, illustrated as a shaft 288 that extends through a rear opening in the support frame 283. The pocket gate 286 is movable within the elongated cavity 285, via the manipulation means, between a fill position shown in FIG. 7, and a dispensing position, shown in FIG. 8. In FIG. 7, the powder material 20 flows under gravity to completely fill the pocket bore 287.

Disposed beneath the distal portion of the volumetric dispensing pocket 282 is a rotary dosing drum 375 that includes a plurality of fill cavities 377 along an outer surface 276, numbered and oriented on the periphery of the dosing drum 395 to fill a number of depressions in a blister sheet 2 position beneath the rotary dosing drum 375.

In FIG. 8, the manipulation means, illustrated as a force exerted upon the shaft 288, moves (slides) the pocket gate 286, and the filled pocket bore 287, to the distal portion of the elongated cavity 285. As the pocket gate 286 moves distally, the upper surface of the proximal portion of the body of the pocket gate 286 covers and closes off the bottom dispensing opening of the elongated bin 271. As the pocket gate 286 continues to move distally, the filled pocket bore 287, filled with the powder material, moves toward registry with the dispensing opening 284. As the filled pocket 287 begins to overlap and move into registry with the dispensing opening 284 of the frame, the powder material with the pocket bore 287 begins to empty out, through the dispensing opening 284, and into a fill cavity 377 disposed in registry beneath the dispensing opening 284 of the frame. Typically, a plurality of the volumetric dispensing pockets 282 are positioned laterally along the length of the elongated supply bin 271, and operated to dispense a dose of powder material into each of a plurality of fill cavities 377 aligned in registry with a corresponding plurality of fill pockets 377 formed into the outer surface 276, and across the width, of the rotary dosing drum 375.

As the rotary drum 275 rotates, each fill cavity 377 revolves toward the fill point. As the fill cavity 377 approaches and aligns in registry with dispensing opening 284, the dose of powder material drops by gravity out of the filled pocket 287, through the dispensing opening 284, and into the respective fill cavity 377.

The rotary dosing apparatus 225 also includes a shell 274 that has an arcuate inner surface that confronts the outer cylindrical surface 276 between the dispensing opening 284 and the discharge point 273 of the apparatus 225, covering the filled cavities **377*f* (fill cavities 377 filled with powder material 20) to prevent spillage of the powder material. The leading edge of the shell 274 provides a means for clearing excess powder dispensed into the fill cavity 377, and leveling off the surface of the powder within the filled cavity 377*f***.

In some embodiments of a rotary dosing apparatus, a vacuum system can be included that applies a vacuum upon the inside surface of the fill cavities 377 to assist in maintaining the powder material charged into the fill cavities 377. The vacuum system may provide independent control to pull or release vacuum for each fill cavity 377. As each fill cavity 377 reaches the discharge point 273, the respective vacuum source for such cavity may be released to allow gravity discharge of the powder material into each depression 4 of the blister sheet 2. In some embodiments, alone or in combination with release of vacuum, a small pulse of air (positive pressure) may be provided to aid gravity discharge of the powder from the fill cavity 377 into the depression 4. In some embodiments, alone or in combination with release of vacuum, gravity discharge of the powder from the fill cavity 377 into the depression 4 may be aided by tapping, vibration, or other mechanical actuation.

In some embodiments, each fill cavity is sufficient in size and depth to hold and dispense a dose of the powder material 20 into each depression 4 of a blister sheet 2, sufficient and effective for forming a powder layer 61.

After each of the filled cavities **377*f* deposits its powder material into an empty depression 4 of the blister sheet 2, the fill cavities 377 of the rotary drum 275 and the blister sheet 2** advance in registry at the same linear speed. Once emptied, the fill cavities advance toward the fill point.

It should be understood that the registering and filling of depressions, and the movement of the pocket bores between the filled and dispensing positions, occurs simultaneously or contemporaneously in the other depressions and volumetric dispensing pocket 282 laterally along the elongated bin 271.

A 3DP system and apparatus can include a second dosing apparatus for dispensing a dose of a second powder material, including a different second powder material, into the depressions, for forming a dosage form that contains two sources, types and compositions of powder material. Additional embodiments of the 3DP system and apparatus can include a third, or additional, dosing apparatus for dispensing a dose of a third powder material, or additional powder material, including a different third powder material, into the depressions, for forming a dosage form that contains three or more sources, types and compositions of powder material.

Other non-limiting examples of a mechanical dosing and/or metering apparatus is described in U.S. Pat. Nos. 9,409,699 and 9,828,119, and US Patent Publications 2017/0322068 and 2018/0031410, the disclosures of which are incorporated by reference in their entireties. Piezo-needle dispensing apparatuses dispense a powder actuated by passing the powder material down a stainless-steel tube using a piezoelectric actuator-driven standing wave. At the dispensing tip of the needle, the standing wave serves to eject the powder material. These devices are effective at delivering low and fixed levels of powder material, delivered with precision. Other non-limiting examples of a mechanical dosing and/or metering apparatus can include a gravimetric powder dispensing/powder dosing apparatus available from ChemSpeed Technologies (https://www.chemspeed.com/flex-powderdose/), the disclosures of which are incorporated by reference in their entireties.

Figure 9:
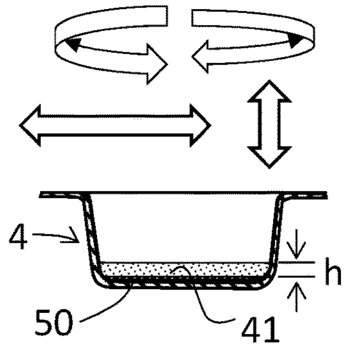
FIG. 9 illustrates various means for leveling a pile of powder material into a substantially uniform layer by shaking and/or oscillating the depression.

In some embodiments, the method and system include a means for leveling a pile of powder material within a depression, into a level or substantially level layer of powder material. FIG. 9 illustrates a step of leveling a pile 40 of a predetermined amount of a powder material 20, within the depression 4, into a substantially uniform layer of powder 41. A pile 40 or other shaped deposit of powder material 20 is transformed into a substantially uniform layer 41 of powder using a leveling means. In the illustrated embodiment of FIG. 9, a leveling means includes a method comprising oscillating, shaking, vibrating, and/or impacting the depression 4, and the pile 40 of powder contained therein, in any one or a combination of laterally, lateral-orbitally, vertically, and vertically-orbitally directions, with a frequency and velocity sufficient to cause the pile 40 of powder to disperse and be spread outwardly over the entire bottom area of the space 5 of the depression 4, and in some embodiments, into a substantially uniform layer 41 of powder. The method forms a first substantially uniform layer 41 of powder, having a predeterminable layer thickness or height h. In a manual system, the packaging and the depression portion thereof can be shaken manually or with a vibrating table.

FIGS. 11 through 15 show an embodiment of a leveling apparatus, comprising a carriage 70 carrying a blister sheet 2, being transported along a conveying track 510 in a powder leveling region and process. In the illustrated embodiment, the conveying track 510 transports the carriage 70 from a powder deposition region, where each of the depressions in the blister sheet includes a pile or load of the powder material, towards a liquid printing region, where the leveled layer of the powder material is printed with a binding liquid. The section of the track 510 passes a powder level station 80, illustrated as a linear rack of teeth 82 or grooves formed along an upper linear edge of a wall 83 secured adjacent to the track 510 by a base 81. The linear rack of teeth 82 is positioned at a vertical height relative to and parallel with the track 510 to engage a toothed gear of a rotary tapping element.

The carriage 70 includes a base 71 affixed to a rack 75 to secure slidingly the carriage 70 to the track 510. The rack 75 is configured to move along the track 510 by a motive means. Non-limiting examples of the motive means can include a belt conveyor, a linked-chain conveyor, a tow conveyor, a screw or auger conveyor, and a wheeled conveyor. The carriage 70 is configured to support a support plate 60, which supports the blister sheet 2. The carriage 70 includes a plurality of wall sections 72 along on lateral side, and a corresponding plurality of wall sections 73 along the opposed lateral side, to define a support space between the wall sections 72 and the wall sections 73 for the support plate 60. The carriage 70 also has a pair of elongated grooves 76 formed longitudinally into the body of the carriage, on opposite sides of the longitudinal centerline. The carriage 70 also have a plurality of (three are illustrated) transverse grooves 77, each extending laterally through the base 71, through both wall sections 72 and 73, and traversing both of the elongated grooves 76.

The support plate 60 includes a matrix of openings 62 in an upper surface 61 that have an opening size and depth to accept in registry the depressions of a corresponding blister sheet 2, with the opening size configured to prevent the depressions of the blister sheet from lateral movement within the openings 62 when the sheet portions of the blister sheet lay upon the upper surface 61 of the support plate 60.

The support plate 60 also includes a pair of elongated grooves 63 formed longitudinally into undersurface of the support plate 60, on opposite sides of the longitudinal centerline of the support plate 60. When the support plate 60 is aligned and supported within the support space between the opposed wall sections 72 and 73, the pair of elongated grooves 63 on the underside of the support plate 60 are aligned and registered above the pair of elongated grooves 76 in the body of the carriage 70.

The carriage 70 also includes a plurality of rotary tapping elements, secured rotatively within and between the base 71 of the carriage 70 and the support plate 60. Each rotary tapping element includes an axle 94 having a tooth gear 96 on one end of the axle 94 and a tapping wheel on the other end.

Figure 14:
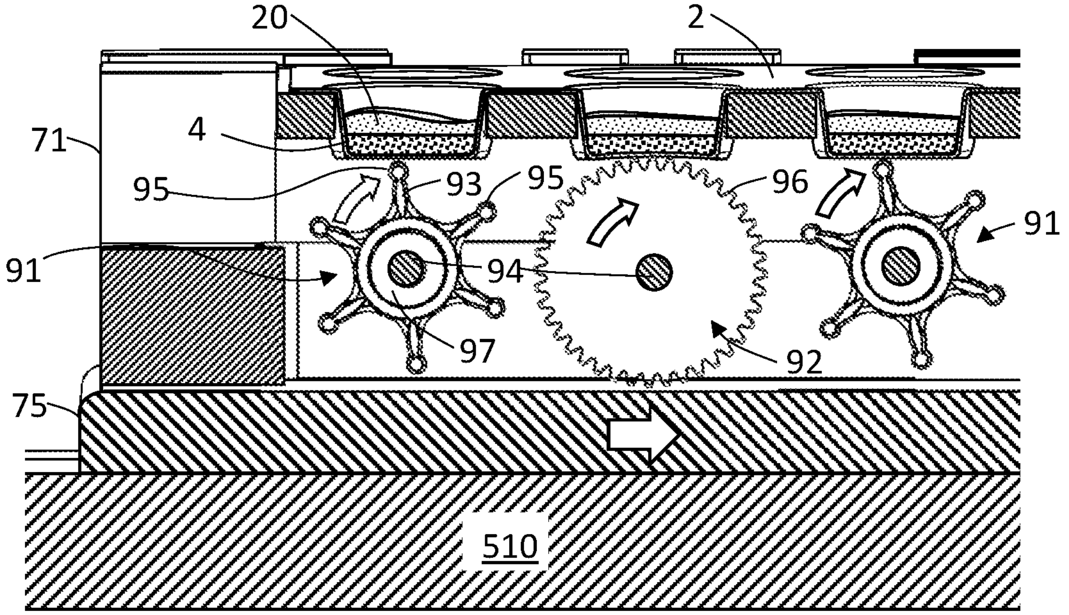
FIG. 14 shows a vertical sectional view of the shuttle carriage, viewed through line 14-14 of FIG. 13, with the tapping means in a first position.

One embodiment of a tapping wheel includes an armed tapping wheel 91 having a plurality, illustrated in FIG. 14 as six, radially-extending arms 93 extending from a central core 97. The number of arms can be any number, for example from 2 to 10, or more. Each arm extends to a distal tip 95 having a fixed radius. In some embodiments, the material of the arms can be a rigid or resilient material, and the shape of the tip 95 can be flat, rounded or pointed. The material and shape of the arms and tips can be selected, in combination with the number of arms, the radius of the tips, and the rotational speed of the tapping wheel, to provide an effective tapping onto the underside of the depressions 4 of the blister sheet to effect a vertical oscillation or vibration of the depression and the powder material therein.

Figure 15:
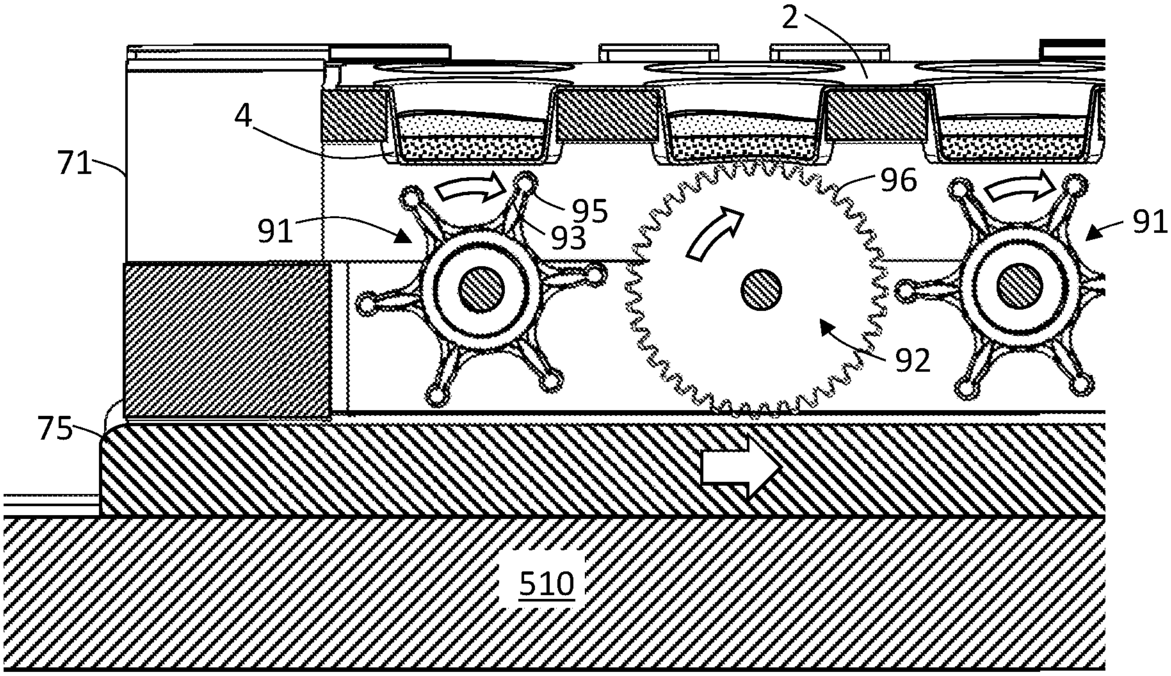
FIG. 15 shows the vertical sectional view of the shuttle carriage of FIG. 14, with the tapping means in a second position.

In some embodiments, the transverse position of the successive arms 93 of the armed tapping wheel 91 can be varied to deliver tapping on the undersurface of the depression across the width (transverse diameter) of the depression 4, so that the undersurface of each depression 4 is impacted or tapped at different lateral positions with each deflection of the depression 4 by the revolving tips 95. The deflection of the undersurface of the depressions 4 is illustrated in FIG. 14, where the tip 95 of the armed tapping wheel 91 deflects the undersurface of the depressions each time an arm 93 passes beneath the depression 4. As the armed tapping wheel 91 continues rotating, the tip 95 rotates out of contact with and deflection of the undersurface of the depression 4, as shown in FIG. 15.

In other embodiments, the transverse width of the tips 95 can extend the full width (transverse diameter) of the depression 4, so that the full undersurface of each depression 4 is impacted or tapped with each deflection of the depression 4 by the revolving tips. In some embodiments, the distance of vertical deflection of the undersurface of the depression 4 of the blister sheet by the tips 93 of the armed tapping wheel 91 can be selected between about 0.5 millimeter to about 6 millimeter, by adjusting the thickness of the support plate 60.

Another embodiment of a tapping wheel includes a toothed gear wheel 92 having a plurality of teeth, and illustrated as forty (40) teeth 96 in FIG. 14, which are spaced along the outer periphery of the toothed gear wheel 92. The number of teeth 96 can be any number, for example from 20 to 60. In some embodiments, the material of the teeth 96 can be a rigid or resilient material, and the shape of the teeth 96 can be rounded or pointed. The material and shape of the teeth 96 can be selected, in combination with the number of teeth, the radius of tips of the teeth, and velocity of the carriage along the track 510 (which effects the rotational speed of the toothed gear wheel 92), to provide an effective tapping onto the underside of the depressions 4 of the blister sheet to effect a vertical oscillation or vibration of the depression and the powder material within. In particular, the frequency of deflections can be effected and controlled by the number of teeth 96 or tips 95, and the rotation speed. The amplitude of the force of a deflection can be controlled by controlling the vertical deflection distance. In some embodiments, the distance of vertical deflection of the undersurface of the depression 4 of the blister sheet 2 by the teeth of the toothed gear wheel 92 can be selected between about 0.5 millimeter to about 6 millimeter, by adjusting the thickness of the support plate 60. In this embodiment, the teeth 96 of the toothed gear wheel 92 deflect the undersurface of the depressions 4 substantially continuously.

The rotary tapping elements are disposed beneath each of the depressions 4 of the blister sheet 2, and as in the illustrated embodiment, any combination of the armed tapping wheel 91 and the toothed gear wheel 92 elements can be used. In other embodiments, all of the rotary tapping elements can have either the armed tapping wheel 91 or the toothed gear wheel 92 elements, or equivalents or variants thereof.

The axles 94 of either the armed tapping wheel 91 and the toothed gear wheel 92 are disposed rotatively within the transverse grooves 77 of the carriage base 71, with the respective tapping wheel (either the armed tapping wheel 91 or the toothed gear wheel 92) disposed rotatively within the adjoining elongated grooves 63 and 76 in the support plate 60 and carriage 70, respectively. The tooth gear 96 on one end of the axle 94 extends beyond the respective wall sections 72 and 73 to register with and engage the rack 75, illustrated as a linear rack of teeth 82 of the wall 83 of the powder level station 80.

As the carriage traverses the powder level station 80, the plurality of tooth gears 96 engage and rotate along the rack of teeth 82 of the wall 83, effecting rotation of the tapping wheels, as illustrated in FIGS. 14 and 15. In the illustrated embodiment, the twelve (12) teeth of the tooth gear 96 and the forty (40) teeth along the rack of teeth 82 of the wall 83 result in each of the tapping wheels rotating 3⅓ full turns in one passing of the carriage 70 traversing the powder level station 80. A typical velocity at which the carriage 70 passes through the powder level station 80 is about 4-8 inches (10-20 cm) per second. In the illustrated embodiment, the rack of teeth 82 of the wall 83 is about 6 inches (15 cm) long, so that the carriage 70 passes through the powder level station 80 in about 1 second, and the rotary tapping elements turn at about 200 revolutions per minute (rpm).

FIGS. 16 through 20 show another embodiment of a leveling apparatus, comprising a carriage 170 carrying a blister sheet 2, being transported along the conveying track 510 in a powder leveling region and process. In the illustrated embodiment, the conveying track 510, similar to the preceding embodiment, can transport the carriage 170 from a powder deposition region towards a liquid printing region, and pass a powder level station 180, illustrated as one or more ramps 182,184 extending upward from a wall 183 secured adjacent to the track 510 by a base 181. The one or more ramps 182,184 have an upper ramped surface 185, and are positioned at a vertical height relative to and parallel with the track 510 to engage extending elements of the carriage 170, described below, as the carriage passes by the powder level station 180. In an alternative embodiment, a cam track can be used.

In this embodiment, leveling of a dose of powder within a depression, or plurality of depressions, can be effected by raising and dropping the depressions or a carriage within which the depressions are secured, to induce a force upon the powder material within the depressions that induces the powder material to settle into a more level state. The degree of leveling can be controlled by altering the number and cycles of raising and dropping, and their frequency, as well as the amount of force or impact when the carriage is dropped. The force at which a carriage or depression drops and strikes a surface can be made by use of gravity (free-fall) or by an external force on the carriage, such as the return force of a biased spring.

The carriage 170 includes a carriage body 174 having one end hingedly attached to one end of a linking member 176, and the other end of the linking member 176 hingedly attached to one end of a base 171. The base 171 is fixed to a rack 175 to secure the carriage 170 to the track 510, the rack 175 being similar to the rack 75 described above. In addition, the base 171 includes a joint member 179 on either end, and in the illustrated embodiment, at the forward (F)-directed end 178.

The carriage body 174 is configured to support a support plate 160, which supports the blister sheet 2. The carriage body 174 includes one or more wall sections 172 along one lateral side, and a corresponding one or more wall sections 173 along the opposed lateral side, to define a support space between the wall sections 172 and 173 for the support plate 160. A set screw 198 threadable through one of the wall sections 172 and 173 can be threaded into contact with a side of the support plate 160, to secure the support plate 160 into a fixed position within the carriage body 174. The carriage body 174 also has a first pair of rotating rollers 191 (or alternatively, cams) that are extended laterally outward from opposite sides at the front end of the carriage body 174, and a second pair of rotating rollers 192 that are extended laterally outward from opposite sides at the rear end of the carriage body 174. The rollers 191,192 can be fixed to opposite ends of rotatable axles that can rotate within the front and rear ends of the carriage body 174, respectively. Alternatively, the rollers 191,192 can be rotatably fixed independently to opposite ends of fixed axles secured at or within the front and rear ends of the carriage body 174, respectively.

The support plate 160 includes a matrix of openings 62 (FIG. 12) in an upper surface 161 that have an opening size and depth to accept in registry the depressions of a corresponding blister sheet 2, with the opening size configured to prevent the depressions of the blister sheet from lateral movement within the openings 162 when the sheet portions of the blister sheet lay upon the upper surface 161 of the support plate 160.

A linking member 176 has a first, rearward (R)-directed end 196 having a joint member 198 that is hingedly attached to a joint member 194 at the rearward (R)-directed end 193 of the carriage body 174. The joint members 194 and 198 both have a transversely-extending bore or bores (not shown in the figures) through which a pin (not shown in the figures) is installed, to form a hinge. The hinge between the first end 196 of the linking member 176 and the rearward-directed end 193 of the carriage body 174 can be formed using any other known hinge means.

The linking member 176 also has a second, forward (F)-directed end 197 having a joint member 199 that is hingedly attached to the joint member 179 at the forward-directed end 178 of the base 171. The joint members 179 and 199 both have a transversely-extending bore or bores (not shown in the figures) through which a pin 189 is inserted, to form a hinge. The hinge between the second end 197 of the linking member 176 and the forward-directed end 178 of the base 171 can be formed using any other known hinge means.

Figure 16:
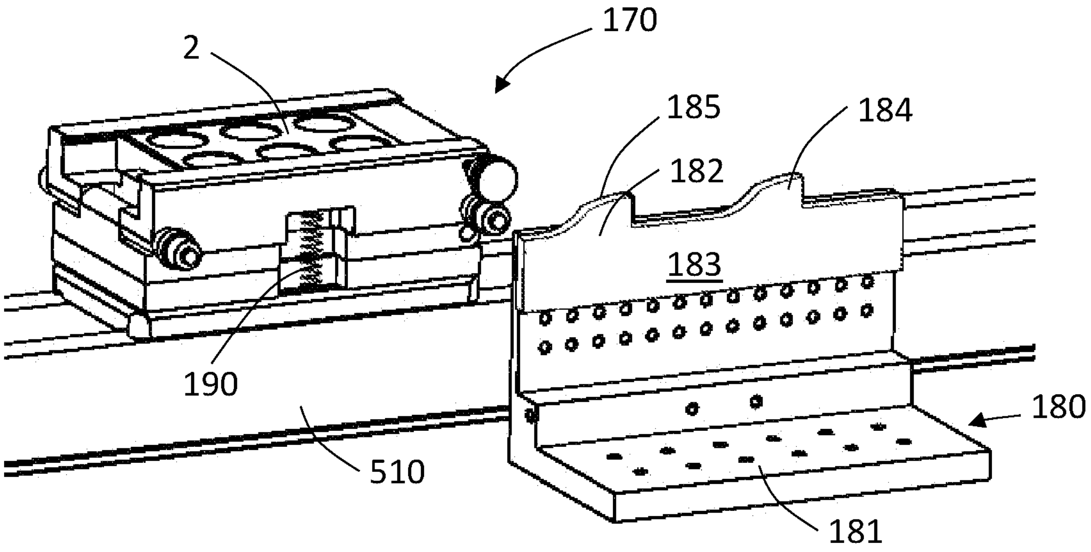
FIG. 16 illustrates a second shuttle carriage operating within a leveling region approaching an elevating means that provides vertical oscillation of a dose of powder material deposited within depressions of a blister sheet.
Figure 17:
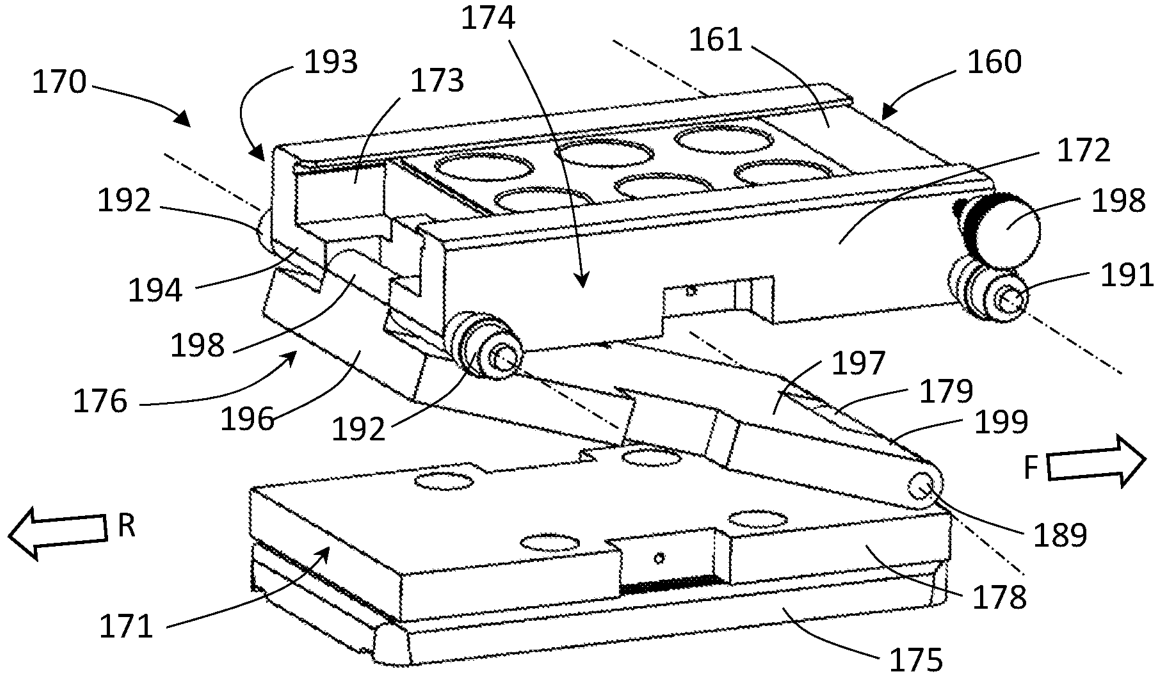
FIG. 17 illustrates the elements of the second shuttle carriage.
Figure 18:
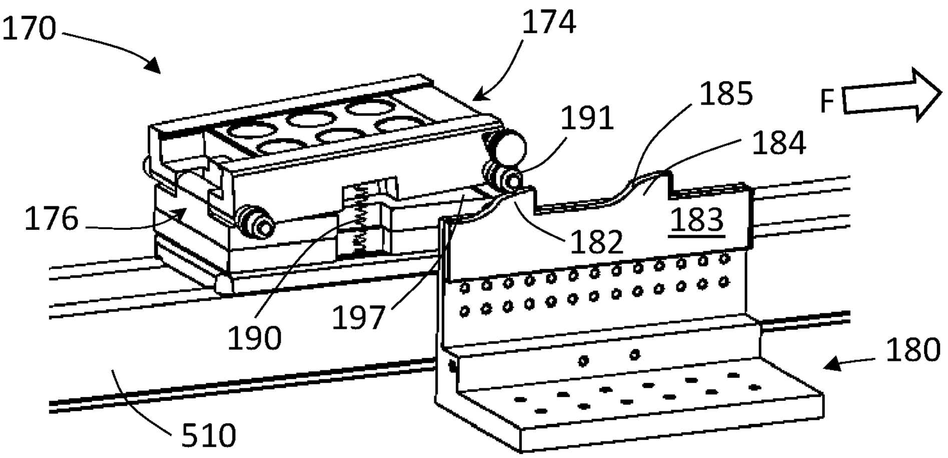
FIG. 18 illustrates a forward end of the second shuttle carriage being raised vertically by a first riser of the elevating means.
Figure 19:
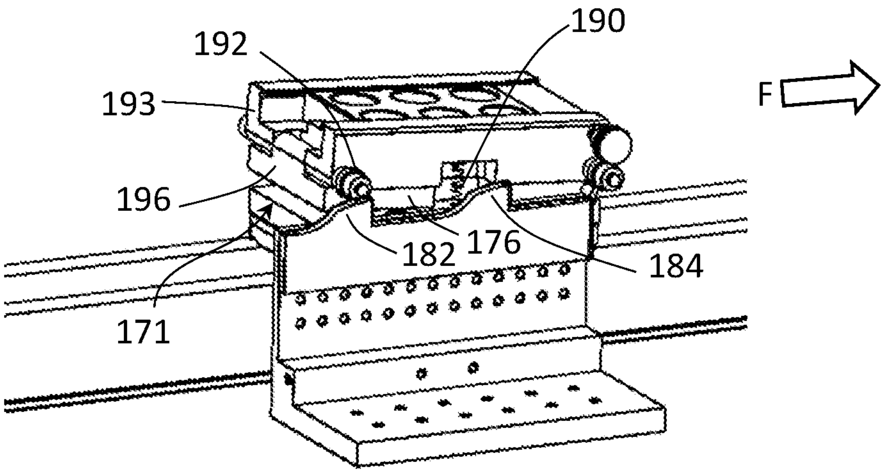
FIG. 19 illustrates the forward end of the second shuttle carriage after dropping off of the first riser, and the rearward end of the second shuttle carriage being raised vertically by a second riser of the elevating means.

The hinges formed between the carriage body 174, the linking member 176, and the base 171 allow for either or both ends of the carriage body 174 to be raised upwardly, from its completely collapsed or flattened position shown in FIG. 16, to a raised or expanded position as shown in FIGS. 18 and 19, as the carriage 170 passes through the powder level station 180.

Optionally, though illustrated in FIG. 16, a linear spring 190 can be secured at its opposite ends to the carriage body 174 at approximately the lateral centerline, and to the base 171 at approximately the lateral centerline. The spring 190 provides a means for biasing the plane of the carriage body 174 toward the plane of the base 171, to ensure that the carriage 170 returns to its collapsed or flattened position from a raised or expanded position. The spring can have a spring constant of about 0.35 to 8 pounds force per inch (88-1400 N/m). Similarly, the spring constant may be chosen in order to enhance the restoring force and provide greater momentum change (impulse) upon deceleration and return of the carriage 170 to its collapsed or flattened position, obtaining or enhancing a leveling effect on any powder.

Figure 20:
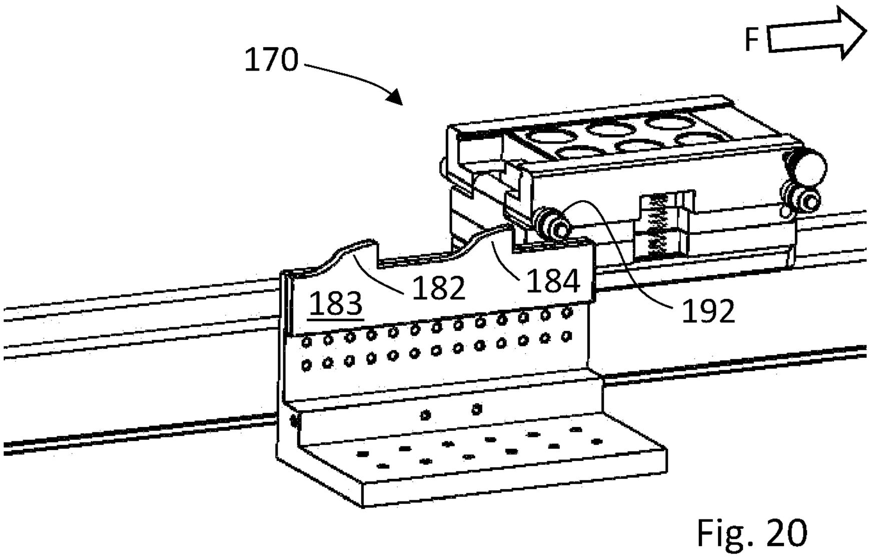
FIG. 20 illustrates the rearward end of the second shuttle carriage after dropping off of the second riser.

FIGS. 18-20 illustrate the carriage 170 as it traverses the powder level station 180. The upper ramped surface 185 of the ramps 182, 184 of the powder level station 180 provides a gradual increase in elevation as the first pair of rotating rollers 191 of the carriage body 174 proceed forward into the powder level station 180 and engage the first ramp 182, ascending to the upper surface of the first ramp 182 as shown in FIG. 18. This causes the forward-directed end of the carriage body 174 to be raised upward, separating from the forward-directed second end 197 of the linking member 176, and exerting an extending force on the spring 190. As the carriage 170 proceeds further forward, the first pair of rotating rollers 191 moves beyond the forward edge of the first ramp 182. Both gravity and the force of the spring 190 drive the forward-directed end of the carriage body 174 downward to impact against the linking member 176 as the first pair of rotating rollers 191 re-engages with an upper surface of the wall 183 between the first ramp 182 and the second ramp 184. The impact in the vertical direction is sufficient to vibrate the carriage 170, including the support plate 160 secured to the carriage body 174, and the depressions 4 and the pile or dose of powder material that has been deposited therein, causing the powder material to momentarily vibrate and partially fluidize, and reducing the variability in height of the surface of the powder material, and increasing the leveling of the powder material with the depression. The first pair of rotating rollers 191 of the carriage body 174 proceeds up and over the second ramp 184 in the same manner, further increasing or improving the leveling of the powder material with the depression.

Similarly, as shown in FIG. 19, the second pair of rotating rollers 192 of the carriage body 174 engages the first ramp 182, ascending to the upper surface of the first ramp. This causes both the rearward-directed end 193 of the carriage body 174 and the rearward (R)-directed end 196 of the linking member 176 to be raised upward, separating it from the rearward-directed end 197 of the base 171, and exerting an extending force on the spring 190. As the carriage 170 proceeds further forward, the second pair of rotating rollers 192 moves beyond the forward edge of the first ramp 182. Both gravity and the force of the spring 190 drive the rearward-directed end of the carriage body 174 downward to impact against the linking member 176 as the second pair of rotating rollers 192 re-engage with an upper surface of the wall 183 between the first ramp 182 and the second ramp 184. As described above, the impact in the vertical direction is sufficient to vibrate the carriage 170, resulting in reducing variability in height of the surface of the powder material, and increasing the leveling of the powder material with the depression. Likewise, the second pair of rotating rollers 192 of the carriage body 174 proceeds up and over the second ramp 184 in the same manner, as shown in FIG. 20, further increasing or improving the leveling of the powder material with the depression.

Other non-limiting examples of mechanical vibrating tables, conveyors are available from the Tinsley Equipment Company, available at https://www.tinsleycompany.com/bulk-process-equipment/vibratory-process-equipment/vibrating-tables/, the disclosure of which is incorporated by reference.

In some embodiments, a layer of powder material that is prepared within a depression has a flat, planar surface, and parallel with the base of the depression. In some embodiments, a layer of powder material that is prepared within a depression can have a uniform thickness with a tolerance. In such embodiments, the thickness of a layer of powder material that is slightly non-uniform in thickness but within the tolerance can be bound with a binding liquid into a bound-powder dosage form. In some embodiments, the non-uniformity in level of the powder material layer can be defined by the variance in thickness of the powder layer from a weight average or target thickness. A minimum thickness in the powder layer and a maximum thickness in the powder layer can have a variance relative to the weight average thickness, where the variance is up to about 25% variance. In some embodiments, the variance is up to about 20% variance, up to about 15% variance, and in some embodiments, up to about 10% variance, and the variance can be at least 5%, at least 10%, at least 15%, or at least 20% variance. For example, a layer of powder material having a weight average (target) thickness of about 0.50 mm can have a thickness with a tolerance of 20%, wherein the powder layer has a minimum and maximum thickness from about 0.40 mm to 0.6 mm, while the binding of the powder material with a binding liquid is still effective. In another example, a layer of powder material having a weight average (target) thickness of about 1.0 mm can have a thickness with a tolerance of 15%, wherein the powder layer has a minimum and maximum thickness from about 0.85 mm to 1.15 mm, while the binding of the powder material with a binding liquid is still effective.

A support plate can be used to secure and support the one or more depressions of the blister pack, including, but not limited to, during powder deposition and layering, binding liquid deposition, solvent removal, and any other process step of the method and system. Ports or openings in the support plate provide a receptacle for receiving and supporting a depression and the blister pack upon the upper surface of the support plate. In some embodiments, a pattern of depressions can be registered with a pattern of openings in a support plate. In some embodiments, the pattern of openings includes a plurality of rows and a plurality of columns. In some embodiments, the openings extend into and through the entire thickness of the support plate. In some embodiments, the openings extend into and only partially through the thickness of the support plate, to provide a blind hole.

Figure 10:
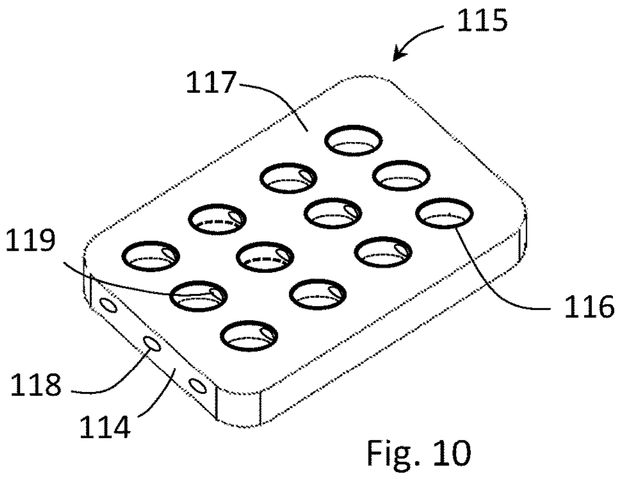
FIG. 10 illustrates a support plate having openings in registry with the pattern of depressions for the blister pack, and a vacuum means for securing a blister sheet to the support plate.

FIG. 10 illustrates an embodiment of a support plate 115 that includes a pattern of openings 116 through the upper surface 117, forming blind holes into the support plate 115. The support plate 115 has three columns and four rows of blind holes 116, and a series of longitudinal entry bores 118 extending from an end edge 114 of the support plate 115, and intermediate bores 119 extending through the thickness along the column of four blind holes 116, and through the material between each of the adjacent openings 116, thereby placing the entry bores 118 and intermediate bores 119 into communication with each blind opening 116 in the column. Application of a vacuum to the entry bores 118 communicates with each blind opening 116 via the intermediate bores 119, to draw and secure the blister pack 1 to the upper surface 117 of the support plate 115.

Figure 28:
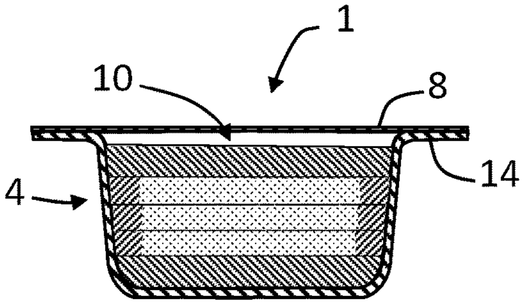
FIG. 28 illustrates a packaged dosage form after applying and sealing a lidding film to the depression.

The aforementioned PCT Patent Publication WO2020-081561 also shows at FIG. 28 a vibratory apparatus for use in providing lateral oscillating of a depression within blister sheet, which is supported within a support plate. The lateral tapping provides leveling and improves the uniformity of the powder material into a layer of powder within the depression. The frequency and degree of rotative oscillation is controlled to provide a frequency and impact force of the oscillation of the base against the support plate to provide effective leveling of the powder layer, without ejecting powder out of the depression or drifting the powder unevenly within the depression.

An alternative apparatus for leveling a pile of powder into a substantially uniform layer of powder within a depression is shown in the aforementioned PCT Patent Publication WO2020-081561, which includes a vertical rotor shaft that is driven by a powered rotating means to rotate a powder level member around the axis of the rotor shaft while being lowered down into the pile of powder material to form the substantially uniform layer of powder within the depression. The powder level member can include a brush assembly including a plurality of brushes attached to and extending down from an under surface of a circular disk. The layering brushes can be made of a material that avoids adhesion of the particles of the powder material, to avoid sticking during operation. In alternative embodiments, the powder level member can include a single horizontal member, including using a blade or a bar, have a curvature within the plane of rotation, and/or have a lower edge that is curved and non-linear, for example, concave or convex, in order to sweep the surface of the pile of powder material into a layer of powder material with the same surface profile.

The present invention can provide a step of applying a binding liquid onto a first or subsequent layer of powder. In a preferred embodiment, the binding liquid is applied using 3D printing methods and techniques, such as those described in U.S. Pat. Nos. 6,471,992, 6,945,638, 7,300,668, 7,875,290, and 8,088,415, the disclosures of which are incorporated by reference in their entireties. In various embodiments, a first predetermined quantity of binding liquid is deposited by spraying droplets of the liquid from the print nozzles of the inkjet printing nozzle assembly. Selected nozzles of the 3D printing assembly are configured to apply droplets or a stream of a binding liquid selectively at the peripheral edges of the first powder layer, thereby wetting the powder at the peripheral edges of the powder layer to form a wetted peripheral coating. The droplets of binding liquid bind particles of the powder material into a cohesive powder-liquid matrix, forming a first layer of wetted powder in a substantially uniform layer.

In a typical embodiment, the binding liquid includes an amount of a solvent that remains in excess in the resulting wetted powder layer, and is preferably removed to form a finished bound powder layer. A liquid removal system can be provided and is adapted to receive one or more blister sheets having one or more layers of wetted powder, or completed 3DP dosage forms, contained within depressions, to remove a liquid there from. A liquid removal system can be a process area through which one or more of the blister sheets are conducted. The liquid removal system can remove or reduce liquid from the incremented printed layers of an in-process 3DP form. Alternatively, the liquid removal system can be another process area not directly associated with the three-dimensional printing system, such as a temporary retaining or storage area wherein three-dimensionally printed blister sheets are placed and dried under ambient conditions. In some embodiments, a liquid removal system is one or more dryers. There are means for heating or applying heat to a wetted powder layer formed within the depression to remove excess solvent liquid, to evaporate the excess liquid solvent to a gas or vapor that is carried away from the drying powder layers. Such means for removing liquid solvent can include various forms of heating the excess solvent in the wetted powder layer, to evaporate the excess solvent liquid into a gas or vapor, including one or more of: convective heat transfer using heated air that is passed over or down toward the wetted powder layer; conductive heat transfer using a heating liquid such as a heated liquid or heated air on the underside of the depressions, to conduct heat through the sheet material of the depression and into the wetted powder layer; and irradiative heating using infrared radiation from a suitable infrared light source that passes down into the depression and/or through the sheet material of the depression and into the wetted powder layer, for example as described in U.S. Pat. Nos. 6,990,748, 6,047,484, and 4,631,837, the disclosures of which are incorporated herein by reference in their entireties.

In some embodiments, a drying apparatus includes a multiplicity of infrared light emitting sources arranged in a pattern, for emitting infrared energy toward an upper surface of a blister sheet. The blister sheet including wetted powder material disposed within depressions is passed into a housing and positioned at determined coordinates. In some embodiments, the pattern and coordinates of the upper surface of the wetted powder material is detected and mapped to form a drying profile. The infrared (IR) light sources are illuminated and controlled to emit the IR light exclusively at the upper surfaces of the wetted powder material. The time and intensity of the IR light emitted is maintained to heat and evaporate the upper surfaces and to evaporate moisture and other solvents from the volume for the wetted powder material. In some embodiments, the IR light emitted onto the wetted powder is controlled using a mask that has a pattern of shaped openings to permit passage of the IR energy. In some embodiments, the light emitted through the mask is focused using refractive material, for example, a lens. In some embodiments, IR light source includes a high-resolution IR light emitter, controlled to emit a pattern of IR light. After each successive wetted powder layer is formed within the depression, a portion or all excess solvent from the binding liquid can optionally be removed from the wetted powder layer or layers, as described above. After an uppermost bound powder layer in formed, the excess solvent can be removed therefrom the uppermost wetted powder layer and from the successive wetted powder layers. In some embodiments, some or all of the wetted powder layers can be formed in sequence, and a single drying step can be performed upon the some or all wetted powder layers for solvent removal. In certain embodiments, the removal of excess solvent may be performed continuously or concurrently during materials deposition.

Figure 2:
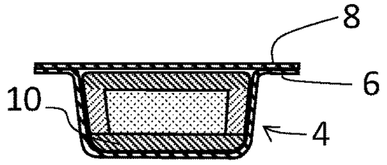
FIG. 2 illustrates a cross-sectional view of a dosage form within a depression covered with the lidding sheet.
Figure 3:
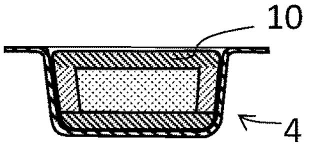
FIG. 3 illustrates a cross-sectional view of a dosage form within a depression, with the lidding sheet removed.

Once the finished dosage forms have been printed within the depressions, such as shown in FIG. 3, the depressions containing the dosage forms can be covered with a lidding sheet to seal the dosage form within the depression 4 of the packaging, such as shown in FIGS. 1 and 2. The finished dosage form, comprising a bound-powder matrix consisting of the plurality of bound-powder layers, has a shape and a size that substantially conforms to the interior space of the depression.

In an embodiment of the invention, the inner surface of the packaging sheet 6 forming the depression 4 can include a release agent. The release agent provides a means for the outer wall 11 and the bottom surface 12 of the dosage form 10 (see FIG. 1), which confront the inner surface of the wall 9 and closed end 7 of the depression 4, respectively, to easily release the dosage form 10 from, or avoid its adhering to, such inner surfaces. The release agent can be a compound that is applied to the inner surface of the depression prior to the dosage printing. A non-limiting example is a coating of Teflon® which releases the dosage form without residual compound remaining on the depression 4. The release agent can also be a compound, an inherent property or applied feature of, the plastic material of the package sheet 6, such as a plastic film laminated to the inner surface of the sheet having adhesion resistance. In certain embodiments, the release agent may be characterized by low surface energy when compared to the surface tension of the depositing liquid, thereby limiting or mediating the extent of wetting on the inner surface of the depression, and inhibiting migration of the binding liquid along the periphery of the dosage form.

In some embodiments, for depositing a binding liquid having a surface tension in the range of about 40 to 50 mN/m, the interior surface of the depression desirably has a surface energy less than 40 mN/m, and more particularly less than 35 mN/m. If a multilaminate cavity material is used, for example a polyvinyl chloride/polychlorotrifluoroethylene (PVC/PCTFE) is chosen, the PCTFE lamina (30.9 mN/m) is desirably placed on the interior surface of the depression, and the PVC lamina (41.5 mN/m) on the exterior of the depression. In general, the surface energy of the release agent (or plastic) is desirably lower than the surface tension of the depositing fluid by 1 mN/m to 5 mN/m, or 5 mN/m to 10 mN/m, or 10 mN/m or more. A listing of common polymers and data on their solid surface energy is shown as http://surface-tension.de/solid-surface-energy.htm.

While the forming of a single dosage form 10 within a single depression 4 has been illustrated, the methods and devices described herein can be used to form a plurality of dosage forms within respective depressions of a packaging material, such as a blister sheet as shown in FIG. 1. An array of blister-type depressions can include any arrangement or pattern of depressions 4, as is well known in the art.

FIGS. 21-28 illustrate an embodiment for forming a dosage form in situ within a depression portion of the packaging, in which at least two different powder compositions are processed in distinct incremental layers.

As described above and illustrated in FIG. 5, an initial, though optional, step is depositing an initial layer 31 of a binding liquid onto the bottom or closed end 7 of the depression 4, to provide binding of an initial powder material that is deposited into the depression 4. In various embodiments, the initial layer 31 of the binding liquid can be deposited by spraying droplets 30 of the binding liquid, for example from print nozzles 32 of an inkjet printing nozzle assembly 33. An initial layer or film of binding liquid 31 ensures that a bottom surface of the dosage form 10 securely bonds the particles along the bottom surface 12. In some embodiments, an excess amount of binding liquid, more than an amount sufficient to at least bind together the particles of the powder material, is used, to form a wetted coating, which when dried or cured forms a hard, resilient bottom coating. In some embodiments, the binding liquid used to form the wetted coating is a different liquid than the binding liquid used for forming the bound powder layers.

In one embodiment, the array of nozzles are stationary, and the depression or depressions are moved horizontally and below the nozzles. In an alternative embodiment, the depression is stationary, and the array of nozzles are passed horizontally over the depression. As the depression is passing below the array of nozzles, selected ones of the nozzles along the array are activated to express droplets only as the corresponding portions of the powder layer pass below, the resulting expression of droplets forming a predetermined pattern of liquid binder over the portions of the powder layer.

In another embodiment, the droplets 34 are applied using a liquid streaming nozzle, which is configured to deposit a volume of the second binding liquid without the precise droplet size control of an inkjet nozzle. Typically, the spray velocity of the droplets of such liquid streaming nozzles are significantly slower than that of the inkjet spraying system. A non-limiting example of a liquid streaming nozzle is an ultrasonic deposition nozzle, available as the AccuMist™ System from Sonotek Corporation, Milton NY. These spray nozzles result in low velocity droplets, which causes less disturbance to powder materials, with minimal overspray and a wide range of volumetric rates and median droplet size (diameter). The spray patterns are available in a variety of patterns, including both wide and narrow conical patterns, and focused linear streams.

In various embodiments, a base powder composition comprises particles that are formed into a base built layer that forms a base of the dosage form. The base powder composition is added into the base of the depression, and formed into a base uniform powder layer. In various embodiments, the base uniform powder layer is formed into the base uniform powder layer a predetermined amount of the base powder composition, as either a volume or a mass weight, is being added into the depression. In a first powder layer added into the depression, the base powder composition is applied onto the closed end 7 of the depression 4. In other various embodiments, a predetermined amount of the base powder composition, as either a volume or a mass weight, is added into the depression, as a non-layered pile, followed by a step of forming the non-layered pile into the base uniform powder layer. An upper surface of the base uniform powder layer is below, and typically well below, the upper rim of the depression. Various methods and means for adding or depositing the base powder composition and forming the base uniform powder layer are described in various other embodiments herein.

In various embodiments, the base powder composition does not comprise an active ingredient, such as an active pharmaceutical ingredient (API) or a medicament. In various embodiments, the base powder composition may optionally comprise an API or medicament, though of a compound type or in a particulate form that is not adversely affected by the binding liquid, and more specifically, by an aqueous binding liquid. In some embodiments, the base powder composition comprises an API or medicament that is not sensitive or is substantially insensitive to contact and processing with the aqueous binding liquid. Non-limiting sensitive APIs can be, as non-limiting examples, amlodipine, felodipine, fesoterodine, isradipine, nifedipine, nimodipine, nisoldipine, clavulante, fosaprepitant, vildagliptin, levothyroxine sodium, betrixaban maleate, ascorbic acid, zinc sulphate, acetyl salicylic acid, cilazapril, and an oral peptides and proteins, and moisture-sensitive drugs as described in WO 2014/138603, the disclosure of which is incorporated by reference in its entirety. A moisture-sensitive drug is one that can exhibit an undesirable change when exposed to a moist environment, including degrading of the drug activity or form, degrading of the drug compound to one or more impurities, and changing the physical characteristics or morphology of the drug.

In some embodiments, the particle comprising an API or medicament is in a coated or agglomerated form, comprising an API particle that is coated with a coating material or agglomerated with other API particles or non-API particles with an agglomerating binder. In some embodiments, the coated or agglomerated particles can provide a controlled release of the API, for example, a sustained release, a delayed release, or a targeted release, and can include as non-limiting examples, an enteric coating, a reverse enteric coating, or other colonic delivery coating. Other API-containing particles can be selected from the group of spray dried granules, amorphous solid dispersions, API particles with permeability enhancers, and co-crystals.

The dosage forms made according to the invention provide protection to, or minimize the effect on, the API or medicament in the coated or agglomerated APT or medicament particles, that can be caused by or results from contact of the binding liquid onto the base powder composition. An effect on the API or medicament can include a loss in activity of the API or medicament, a reduction or loss in taste masking of the API or medicament, a reduction or loss in any barrier or control effect that the coating material or agglomerating material for the API or medicament, during or after orodispersion and ingestion of the dosage form. In some embodiments, the coating material or agglomerating material comprises an enteric coating.

Figure 21:
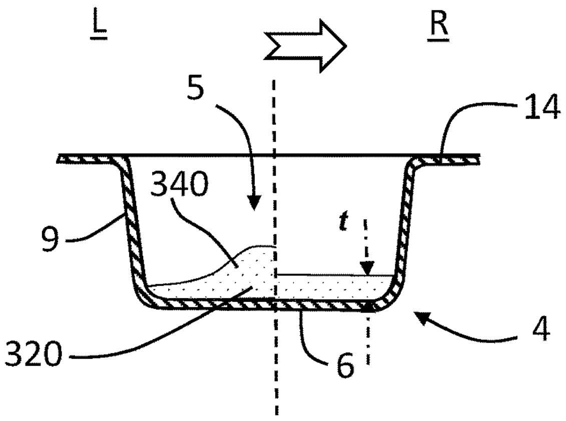
FIG. 21 illustrates a depression being filled with a dose of a first powder composition, and then leveled into a base powder layer.

FIG. 21, on the left (L) side, illustrates a step of depositing a first pile 340 of a first powder composition 320 comprising particles that has been deposited within the depression 4 or into each of a plurality of depressions. The first powder composition 320 can comprise the base powder composition. The first pile 340 is dispensed as a predetermined amount the first powder composition 320 from a powder dispensing means or apparatus as described herein, which can include a predetermined volumetric amount of the powder or a predetermined mass amount of the powder, deposited onto the closed end 7 of the depression 4.

FIG. 21, on the right (R) side, illustrates a step of leveling a pile of powder material in situ within the depression 4 into a base powder layer 341 that is uniformly level or having a uniform thickness t, using a leveling means or apparatus as described herein, causing the pile 340 to disperse and be spread outwardly over the entire bottom or plan area of the closed end 6 of the depression 4, and in preferred embodiments, into the substantially uniform base powder layer 341. The base powder layer 341 has a uniform thickness, and an upper surface of the base powder layer 341 is below an opening into the depression that if bounded or defined by an upper rim 14 of the depression 4.

In various embodiments, a layer of powder material that is prepared within a depression can have a uniform thickness with a tolerance as described herein.

Figure 22:
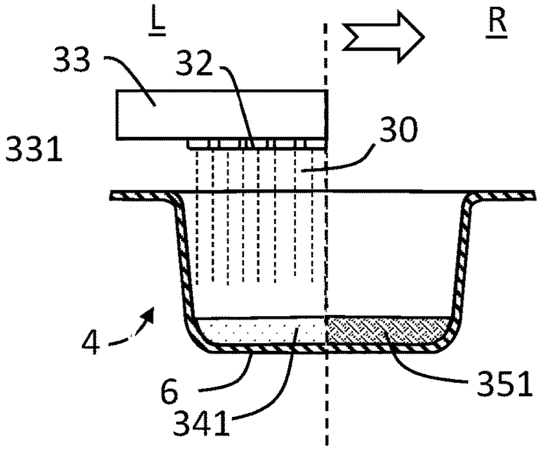
FIG. 22 illustrates the depression with the base powder layer formed from the first powder composition, and printed with a first printing liquid in a continuous pattern to form a wetted powder base powder layer.

FIG. 22, on the left (L) side, illustrates a step of applying a first binding liquid into the space 5 and onto the first powder layer 341. In the illustrated embodiment, a first predetermined quantity of first binding liquid is deposited by spraying droplets 30 of a first liquid composition 331 from the print nozzles 32 of the inkjet printing nozzle assembly 33. The droplets 30 of first binding liquid bind in situ the particles of the first powder composition of the first powder layer 341 into a more cohesive powder-liquid matrix, forming a first layer of wetted powder 351 in a substantially uniform layer, shown in the right (R) side of FIG. 22, with an upper surface well below the opening into or the upper rim 14 of the depression. The droplets 30 of the first liquid composition 331 are dispersed in a continuous or solid pattern, for example a circular pattern, corresponding to the plan area of the first powder layer 341, across the entire plan area and through the thickness of first powder composition of the first powder layer 341.

In a typical embodiment, the first binding liquid includes an amount of a solvent that remains in excess in the resulting base wetted powder layer 351, and is preferably removed to form a finished bound first powder layer, using a solvent removal means and apparatus, such as a drying means or apparatus, as described herein. In other various embodiments, the excess solvent remains in the base wetted powder layer 351, prior to applying a further powder composition. In other various embodiments, the excess solvent is removed (dried) at the conclusion of the forming of the base wetted powder layer 351, before proceeding to apply a further powder composition amount or layer.

In various embodiments, when the first powder composition does not contain an API, or contains an API that is not a sensitive API, or contains particles that do not comprise a sensitive particle comprising an API, the use and application amount of the first binding liquid permits forming a stable, solidified or resilient base coating portion for the dosage form. A sensitive API can otherwise be affected by the application of a binding liquid, particularly an aqueous binding liquid, resulting in a reduction in the API's activity, or the organoleptic characteristics of the API as a particle or of particles comprising the API, or the pharmacodynamics of the API, such as delayed, controlled, or extended rate or amount of release of the API within the one or more segments of the gastrointestinal system following orodispersion in the mouth and ingestion.

A first binding liquid applied to the base powder layer can be a solution or suspension, and can comprise an aqueous carrier, nonaqueous carrier, organic carrier or a combination thereof. The aqueous carrier can be water or an aqueous buffer, or combinations of water with one or more alcohols. The nonaqueous carrier can be an organic solvent, low molecular weight polymer, oil, silicone, other suitable material, alcohol, ethanol, methanol, propanol, isopropanol, (poly)ethylene glycol, glycol, other such materials or a combination thereof. Other binding liquid component and composition as described or incorporated by reference herein can be used.

In various embodiments, an additional base powder layer can be deposited and leveled over the base powder layer 341, substantially as provided for the base powder layer 341, and the first binding composition 331 is deposited to form and additional base wetted powder layer 351 in a substantially uniform layer.

Figure 23:
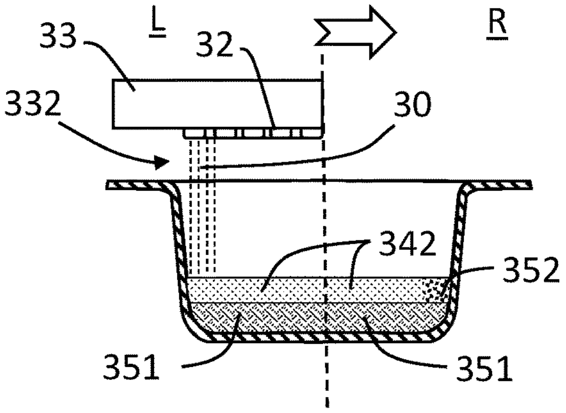
FIG. 23 illustrates the depression with a second powder composition formed into a first intermediate powder layer, and printed with a second printing liquid in a pattern at least upon a peripheral portion to form the first intermediate powder layer with a peripheral band of wetted powder.

FIG. 23, on the left (L) side, illustrates a second powder composition 321 comprising particles that has been deposited in a predetermined amount into the depression, covering the base wetted powder layer 351, and formed in situ into an intermediate powder layer 342 having a uniform thickness. The intermediate powder layer 342 has a uniform thickness t2, which may be the same or different from the uniform thickness of a base powder layer, and an upper surface of the intermediate powder layer 342 is below the opening into or the upper rim 14 of the depression 4. Also illustrated are droplets 30 of a second binding liquid 332 are dispensed from only a portion of the nozzles 32, specifically in a pattern that applies the second binding liquid 332 in an annular peripheral pattern on the intermediate powder layer 342, to bind in situ the particles at the annular periphery of the intermediate powder layer 342, to form a peripheral band 352 of wetted powder through the uniform thickness t2, and unwetted particles of the second powder composition in an interior or central portion of the intermediate powder layer 342, as shown in the right (R) side of FIG. 23.

It should be understood that a layer of wetter powder formed over top of a preceding layer of wetted powder can result in a unitary, single layer of wetted powder that may have a visible boundary, or may not have a visible boundary, at the interface of the two wetted layers. Similarly, after the removal of excess liquid or solvent of the binding liquid, as described below, a bound-powder layer formed over top of a preceding bound-powder layer can result in a unitary, single layer of the bound powder that may have a visible boundary, or may not have a visible boundary, at the interface of the two bound-powder layers.

The thickness 12 of the intermediate powder layer 342 can be the same or different than the thickness t of a base powder layer 341. In various embodiments, the thickness t2 of the intermediate powder layer 342 is 25% or more and up to 200%, for example 50% or more, 100% or more, and up to 150%, of the thickness t of a base powder layer 341.

In various embodiments, the second powder composition contains a sensitive API in particle form, or contains particles that comprise a sensitive API, or both. As described above, a sensitive API and sensitive particle comprising an API, are affected by the application of a binding liquid in an amount sufficient to form the intermediate powder layer into a more cohesive powder-liquid matrix, and may be affected by a reduction in the API's activity, or the organoleptic characteristics of the API as a particle or of particles comprising the API, or the pharmacodynamics of the API, such as the rate of sustained, delayed or targeted release of the API within the gastrointestinal system following orodispersion and ingestion. In various embodiments, the dosage form is design and specified to contain a target minimum active amount of the sensitive API. In the illustrated embodiment, when employing an intermediate uniform powder layer that contains a sensitive API or particles comprising a sensitive API, the effect of the application of the second binding liquid on the full mass of the content is minimized by limiting the application of the second binding liquid to the outer peripheral thickness of the intermediate powder layer, thus significantly restricting the portion of the API in the intermediate powder layer placed into contact with the second binding liquid.

The selection for the amount (saturation) of the second binding liquid (per unit mass of the second powder composition being wetted) and the width of the peripheral band of the intermediate powder layer wetted with the second binding liquid provides sufficient bonding and attachment of the peripheral band 352 of wetted intermediate powder layer to the wetted base powder layer 351 below, as illustrated on the right (R) side of FIG. 23, and the formation of a stable, solidified or resilient sidewall segment 368 after a drying stage for the dosage form, as shown in FIG. 66.

The second binding liquid applied to the intermediate powder layer can be a solution or suspension, and can comprise an aqueous carrier, nonaqueous carrier, organic carrier or a combination thereof. The second binding liquid can be the same as or substantially the same as the first binding liquid.

Figure 24:
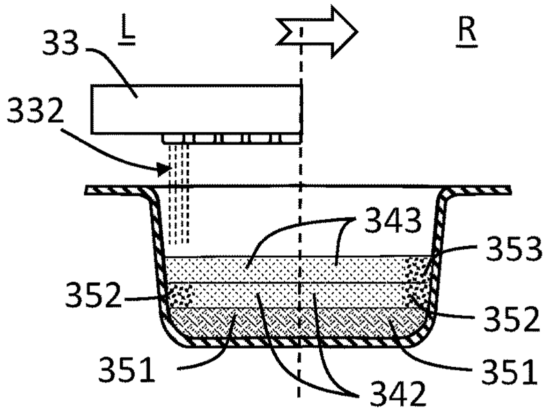
FIG. 24 illustrates the depression with a second intermediate powder layer formed from the second powder composition, formed onto the first intermediate powder layer, and printed with the second printing liquid in a pattern at least upon a peripheral portion to form the second intermediate powder layer with a peripheral band of wetted powder.

FIG. 24, on the left (L) side, shows a second deposited-and-leveled intermediate powder layer 343 over the intermediate powder layer 342 and its peripheral band 368 of wetted powder, and the dispensing of the second binding liquid 332 in a pattern that applies the second binding liquid 332 in an annular peripheral pattern on the second intermediate powder layer 343, to bind in situ the particles at the annular periphery of the second intermediate powder layer 343, to form a peripheral band 353 of wetted powder through the uniform thickness, and unwetted particles of the second powder composition in an interior portion of the second intermediate powder layer 343, as shown in the right (R) side of FIG. 24. The thickness of the second intermediate powder layer 343, and the saturation amount and the width of the peripheral band of the second intermediate powder layer 343 wetted with the second binding liquid, is selected to provide sufficient bonding and attachment of the peripheral band 353 of wetted intermediate powder layer to the peripheral band 352 of wetted intermediate powder layer below, and can be the same or different from that used on the intermediate powder layer 342.

Figure 25:
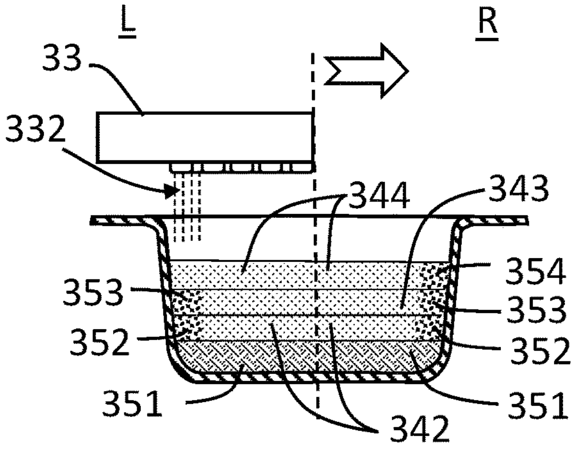
FIG. 25 illustrates the depression with a third intermediate powder layer formed from the second powder composition, formed onto the second intermediate powder layer, and printed with the second printing liquid in a pattern at least upon a peripheral portion to form the second intermediate powder layer with a peripheral band of wetted powder.

Likewise, FIG. 25, on the left (L) side, shows a third deposited-and-leveled intermediate powder layer 344 over the intermediate powder layer 343 and its peripheral band 368 of wetted powder, and the dispensing of the second binding liquid 332 in a pattern that applies the second binding liquid 332 in an annular peripheral pattern on the third intermediate powder layer 344, to bind in situ the particles at the annular periphery of the third intermediate powder layer 344, to form a peripheral band 358 of wetted powder through the layer thickness, and unwetted particles of the second powder composition in an interior portion of the third intermediate powder layer 344, as shown in the right (R) side of FIG. 25. The thickness of the third intermediate powder layer 344, and the saturation amount and the width of the peripheral band of the third intermediate powder layer 344 wetted with the second binding liquid, is selected to provide sufficient bonding and attachment of the peripheral band 354 of wetted intermediate powder to the peripheral band 353 of wetted intermediate powder layer below, and can be the same or different from that used on the first, second or third intermediate powder layers 341, 342 or 343. In various embodiments, additional intermediate powder layers of the second powder composition can be deposited, leveled, and printed, where the printing can be of an annular peripheral band pattern, or of a continuous or solid pattern. In various embodiments, an intermediate powder level, that being a powder layer deposited and leveled over the base bound powder layer, can comprise the first powder composition (a powder composition not containing an API, or not containing a sensitive API or sensitive particle comprising an API).

In various embodiments, a subsequent layer of a fourth powder composition, different from the second powder composition, may be substituted for the second powder composition, in one or more of the intermediate powder layers.

Figure 26:
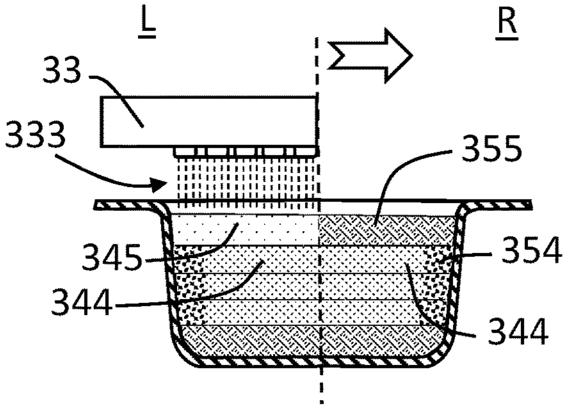
FIG. 26 illustrates the depression with a cap powder layer formed from a third powder composition, and printed with a third printing liquid in a continuous pattern to form a wetted cap powder layer, to form a bounded-powder dosage form with an unbounded powder core.
Figure 27:
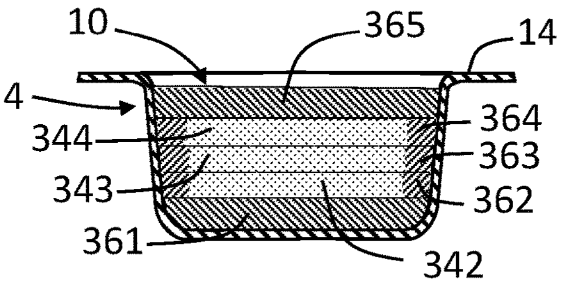
FIG. 27 illustrates a finished dosage form after drying of the bounded-powder dosage form, formed in situ within the packaging depression, containing a first powder composition and a different second powder composition.

FIG. 26, on the left (L) side, illustrates applying and leveling in situ a third powder composition into a cap powder layer 345, over top of and completely covering the upper surface of the third intermediate powder level 344 and its peripheral band 354 of wetted and bound powder, and applying a third binding liquid onto the upper-most cap powder layer 345. In the illustrated embodiment, a first predetermined quantity of a third binding liquid is deposited by spraying droplets 30 of a third liquid composition 333 from the print nozzles, to bind in situ the particles of the third powder composition of the cap powder layer 345 into a cohesive powder-liquid matrix, and forming a cap wetted powder layer 355 with a substantially uniform thickness, shown in the right (R) side of FIG. 26, with an upper surface illustrated as below the opening into or the upper rim 14 of the depression. The droplets 30 of the first liquid composition 331 are dispersed in a continuous or solid pattern, for example a circular pattern, corresponding to the plan area of the cap powder layer 345, across the entire plan area and through the thickness of third powder composition of the cap powder layer 345.

In various embodiments, the cap powder composition comprises particles that are formed into a cap bonded layer that forms a cap or top covering of the dosage form. The cap powder composition does not comprise an active pharmaceutical ingredients (APIs) or a medicament. In various embodiments, the cap powder composition comprises an API or medicament that is not sensitive or is substantially insensitive to contact and processing with the aqueous binding liquid. The cap powder composition can be the same as the base powder composition.

Figure 29:
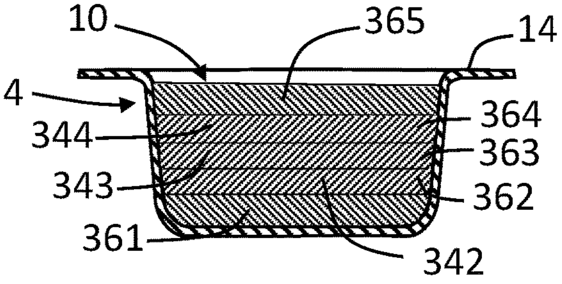
FIG. 29 illustrates the depression with an alternative finished dosage form by which the first, second and third intermediate powder layers are printed across their entire surfaces to form first, second and third intermediate wetted powder layers.

In some embodiments, the pattern and quantity of the binding liquid can be applied cover substantially the entire area of the intermediate powder layers of the second powder composition, to form a liquid-continuous wetted powder, as shown in FIG. 29.

The third binding liquid applied to the cap powder layer can be a solution or suspension, and can comprise an aqueous carrier, nonaqueous carrier, organic carrier or a combination thereof. The third binding liquid can be the same as or substantially the same as the first binding liquid. The selection for the amount (saturation) of the third binding liquid (per unit mass of the third powder composition of the cap powder level being wetted) provides sufficient bonding and attachment of a peripheral portion of wetted cap powder layer 355 to the peripheral band 354 of the wetted intermediate powder layer below, as illustrated on the right (R) side of FIG. 26, and the formation of a stable, solidified or resilient cap layer 365 after a drying stage for the dosage form, as shown in FIG. 67.

The thickness t3 of the cap powder layer 345 can be the same or different than the thickness t of a base powder layer 341, or of any thickness t2 of an intermediate powder layer 342-344. In various embodiments, the thickness t2 of an intermediate powder layer is 25% or more and up to 200%, for example 50% or more, 100% or more, and up to 150%, of the thickness t3 of a cap powder layer 345.

Figure 30:
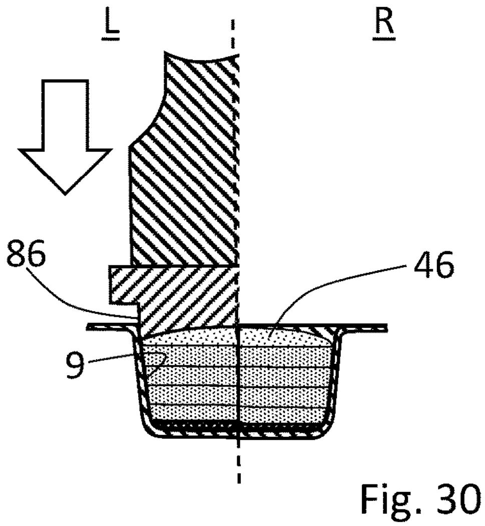
FIG. 30 illustrates a punch positioned into the depression, and pressing down on the upper surface of the powder layer, forming a shaped convex upper surface of the uppermost powder layer.

In various embodiments, after depositing and optionally leveling the cap powder layer, and preceding the printing of the layer with the third binding liquid, an optional step of forming the cap powder layer can be performed, including tamping the last-deposited cap powder layer into a last-formed powder layer having a formed upper surface, as described herein and illustrated in the left (L) side of FIG. 30, to provide a dosage form with a convex upper surface of the uppermost powder layer as illustrated in the right (R) side of FIG. 30. Non-limiting examples of a tamping device, such as a punch, are described in International Publication WO2017/034951, the disclosure of which is incorporated by reference in its entirety. In the illustrated embodiment, the cavity shape is a concave circle, but in other embodiments can be a concave oval, square rectangular, or any other geometrical shape. Alternatively, after printing of the cap powder layer with the third binding liquid, an optional step of forming the wetted cap powder layer can be performed, including tamping the last-deposited cap powder layer into a last-formed wetted powder layer having a formed upper surface.

The wetted powder portions of powder layers, after drying of any excess solvent or liquid, are formed into stable, solidified or resilient peripheral layers. Each wetted powder layer can be processed separately, or in groups of two or more layers, to remove excess binder solvent.

In some embodiments, the punch can be lowered into contact with the powder and advanced based on a detected or measured linear force or pressure on the punch, the extent of linear force or pressure effecting the degree of tamping and/or leveling of the deposited powder layer. In some embodiments, the punch 88 is rotated, as illustrated in FIG. 69, in one rotational direction, as the punch is being lowered. The rotation of the punch 88 while lowering improves the uniformity of depth of the powder layer, and the uniformity of areal tamping of the powder. The movement of the punch 88 can be controlled by any control system known in the art. After the punch 88 is raised, the depression 4 containing the bound powder layers and the shaped top powder layer 46 can be moved to a printing region, where binding liquid can be applied onto the convex-shaped powder material layer 46 to form the last, uppermost bound powder layer 157.

In an alternative embodiment, a punch can be used to shape an uppermost wetted powder layer, after the printing of a layer of powder material, and prior to any drying by evaporation of excess solvent. As described in International Publication WO2017/034951, an automated tamping apparatus can be used for tamping a plurality of dispensed powder layers within depressions.

Generally, a 3DP equipment assembly and/or apparatus can comprise various subsystems including one or more three-dimensional printing build systems, and optionally one or more liquid removal systems. The system can comprise one or more three-dimensional printing build systems, one or more liquid removal (drying) systems and optionally one or more other systems. In some embodiments, the equipment assembly can comprise one or more (sub) systems selected from the group consisting of one or more upper punch systems, one or more control systems, and one or more inspection systems. For example, in certain embodiments of a depression 3DP system, it is not necessary to have a harvesting system since substantially all of the powder material entering a depression is incorporated into a respective dosage form within the depression. Similarly, in certain embodiments of a depression 3DP system, it is not necessary to eject the formed tablets, transport them, and/or feed them into separate packaging, since the tablets are forming in situ in the packaging.

The invention claimed is:

1. A method of forming a dosage form within a portion of a packaging for the dosage form, comprising the steps of:

(1) providing a portion of a packaging for the dosage form, the portion of the packaging comprising at least one depression having an upper rim;

(2) forming in situ within the at least one depression a first powder composition comprising particles, into a base powder layer, wherein an upper surface of the base powder layer is below the upper rim of the depression;

(3) depositing a first binding liquid in a continuous pattern on the base powder layer, to bind the particles of the base powder layer to form a base wetted powder layer;

(4) forming in situ within the at least one depression a second powder composition comprising particles into an intermediate powder layer having a uniform thickness, wherein an upper surface of the intermediate powder layer is below the upper rim of the depression, and wherein the intermediate powder composition is different from the base powder composition;

(5) depositing a second binding liquid in a pattern on the intermediate powder layer along the periphery of the intermediate powder layer, to bind the particles at least along the annular periphery of the intermediate powder layer to form an intermediate wetted powder layer having wetted powder particles at least along the annular periphery of the intermediate wetted powder layer;

(6) forming within the at least one depression a third powder composition comprising particles into a cap powder layer having a uniform thickness, wherein an upper surface of the cap powder layer is at or below the upper rim of the depression;

(7) depositing a third binding liquid in a continuous pattern on the cap powder layer, to bind the particles of the cap powder layer to form a cap wetted powder layer; and (8) drying one or more of the base wetted powder layer, the intermediate wetted layer, and the cap wetted layer, to remove a portion of a solvent contained within the binding liquid.

2. The method according to claim 1, wherein the base powder layer has a uniform thickness, and the intermediate powder layer has a uniform thickness.

3. The method according to claim 2, wherein the intermediate wetted powder layer includes unwetted powder particles of the intermediate powder layer in an interior portion of the intermediate wetted powder layer.

4. The method according to claim 1, wherein the second binding liquid is deposited across substantially the entire area of the intermediate powder layer.

5. The method according to claim 1, wherein the second powder composition contains a moisture-sensitive active pharmaceutical ingredient (API) or a particle comprising a moisture-sensitive API.

6. The method according to claim 5, wherein at least one of the first powder composition and the third powder composition does not contain an API, and does not contain a moisture-sensitive API or a particle comprising a moisture-sensitive API.

7. The method according to claim 6, wherein the moisture-sensitive API comprises a coated API that is coated with a coating material, and the particle comprising the moisture-sensitive API comprises an agglomerated API that is agglomerated with an agglomerating material.

8. The method according to claim 1, wherein the first binding liquid and the third binding liquid are the same liquid composition, and the first powder composition and the third powder composition are the same powder composition.

9. The method according to claim 1, wherein the step of forming the base powder layer comprises depositing the first powder composition as the base powder layer.

10. The method according to claim 9, further including, prior to placing the first powder composition within the at least one depression, a step of depositing a layer of a binding liquid onto the closed end of the depression.

11. The method according to claim 10, wherein the placing of the first powder composition comprises depositing a predetermined amount of the first powder composition into the depression, and forming the deposited, predetermined amount of the first powder composition into the base powder layer.

12. The method according to claim 10, wherein the placing of the intermediate powder composition comprises depositing the second powder composition as the intermediate powder layer.

13. The method according to claim 12, wherein the placing of the intermediate powder composition comprises depositing a predetermined amount of the second powder composition into the depression, and forming the deposited, predetermined amount of the second powder composition into the intermediate powder layer.

14. The method according to claim 13, wherein the placing of the third powder composition comprises depositing the third powder composition as the cap powder layer.

15. The method according to claim 14, wherein the placing of the third powder composition comprises depositing a predetermined amount of the third powder composition into the depression, and forming the deposited, predetermined amount of the third powder composition into the cap powder layer.

16. The method according to claim 1, wherein the step of drying the one or more of the base wetted powder layer precedes the step of placing the second powder composition, and the step of drying the one or more of the intermediate wetted powder layer precedes the step of placing the third powder composition.

* * * * *